United States Patent [19]

Enquist et al.

[11] Patent Number: 5,037,742
[45] Date of Patent: Aug. 6, 1991

[54] PSEUDORABIES VIRUS RECOMBINANTS AND THEIR USE IN THE PRODUCTION OF PROTEINS

[75] Inventors: Lynn W. Enquist, Greenville; Alan K. Robbins; Mary E. Whealy, both of Wilmington, all of Del.

[73] Assignee: E. I. du Pont de Nemours and Company, Wilmington, Del.

[21] Appl. No.: 886,691

[22] Filed: Jul. 18, 1986

[51] Int. Cl.$^5$ .......................... C12P 21/00; C12N 7/00
[52] U.S. Cl. ............................. 435/69.1; 435/69.3; 435/235.1; 435/172.3; 435/320.1; 935/32; 935/27; 935/57; 935/70; 935/60
[58] Field of Search .............. 435/68, 70, 235, 172.3, 435/948, 320, 69.1, 195, 320.1; 935/27, 32, 57, 60, 70

[56] References Cited

U.S. PATENT DOCUMENTS 4,514,497  4/1985  Kit et al. ............................. 435/235
4,680,176  7/1987  Berns et al. .......................... 424/89
4,711,850  12/1987  Kit et al. ............................. 435/68

FOREIGN PATENT DOCUMENTS 0074808  3/1983  European Pat. Off. .
0162738  11/1985  European Pat. Off. ........... 435/69.1

OTHER PUBLICATIONS

CA 104:32830c 1988.
CA 97:195467r 1985.
Maniatis et al., *Molecular Cloning* CSH Press 1982 pp.
Talmadge et al., Construction of Plasmid Vectors With Unique Pst I Cloning Sites in a Signal Sequence Coding Region, Gene 12:235 (1980).
Hu et al., Expression of AIDS virus envelope gene in recombinant vaccinia viruses, Nature 320:537 (1986).
Chakrabarti et al., Expression of HTLV III envelope gene by a recombinant vaccinia virus, Nature 320:535 (1986).
Frischauf et al., Lambda Replacement Vectors Carrying Polylinker Sequences, J. Mol. Biol. 170:827 (1983).
Desrosiers et al., Synthesis of Bovine Growth Hormone in Primates by Using a Herpes Virus Vector, Mol Cell Biol. 5:2796 (1985).
Mackett et al., General Method for Production and Selection of Infectious Vaccinia Virus Recombinants Expressing Foreign Genes, J. Virol 49:857(1984).
Shih et al., Expression of hepatitis B virus S Gene by Herpes Simplex virus type 1 vectors carrying α and β-regulated gene chimeras PNAS 81:5867 (1984).
Wathen et al., Characterization and Mapping of a Nonessential Pseudorabies virus glycoprotein, J. Virol 58:173 (1986).
Mettenleiter et al., Pseudorabies virus avirulent strains fail to express a major glycoprotein, J Virol 56:307 (1985).
Robbins, et al., *J. of Virology*, vol. 58, No. 2 (1986).
Walthen et al. *J. of Virology*, Vol. 58, pp. 173–178 (1986).
Ben-Porat et al., "Molecular Biology of Pseudorabies Virus" in *The Herpes Viruses*, Roizman, ed., vol. 3, Chapter 3, pp. 105–163 (Plenum Press, New York, 1985).
Holland et al., *J. of Virology*, vol. 52, pp. 566–574 (1984).
Homa et al., *J. of Virology*, vol. 58, pp. 281–289 (1986).
Marlin et al., *J. of Virology*, vol. 53, pp. 128–136 (1985).
Roizman et al., *Science*, vol. 229, pp. 1208–1214 (1985).
Holland et al., *J. of Virology*, vol. 46, pp. 649–652 (1983).
Desrosiers et al., *Molecular and Cellular Biology*, Vol. 5, pp. 2796–2803.
Shih et al., *Proc. Natl. Acad. Sci. USA*, Vol. 81, pp. 5867–5870, (1984).
*Mammalian Cell Technology*, pp. 39–55, Thilly, ed. (Butterworth Publishers, Stoneham, MA, 1986).
Moss et al., *Nature*, vol. 311, pp. 67–69.
Smith et al., *Proc. Natl. Acad. Sci. U.S.A.*, vol. 80, pp. 7155–7159 (1983).
Moss, *Banbury Report 22—Genetically Altered Viruses and the Environment*, Fields et al., eds. (Cold Spring Harbor Laboratory, Cold Spring Harbor, N. Y., 1985).

*Primary Examiner*—Robin L. Teskin

[57] ABSTRACT

Recombinant pseudoviruses and their use in the production of proteins having medical, agricultural and industrial utilities are discussed.

13 Claims, 18 Drawing Sheets

FIG. 2

```
              CGC CGC CGC GCA CGT GAC GCG GGC CCT GCT GGT GCA GGC GTA    84

CGT GAC CGT CGC CAT GTG CGC CAC TAG CAT TAA ATC CGT TTC   126

CTG ATT CAC GCC CAC GCT CGC GCG TTT TTA AAA CCG CGA TGG   168

GGG GAC GGG GGG CCA TTC GCA CGC GCC ATG GCC TCG CTC GCG   210
          1                                       MET Ala Ser Leu Ala

CGT GCG ATG CTC GCT CTG CTG GCG CTC TAC GCG GCG GCC ATC   252
          6   Arg Ala MET Leu Ala Leu Leu Ala Leu Tyr Ala Ala Ala Ile

GCC GCG GCG CCG TCG ACC ACG ACG GCG CTC GAC ACG ACG CCC   294
         20   Ala Ala Ala Pro Ser Thr Thr Thr Ala Leu Asp Thr Thr Pro

AAC GGG GGC GGC GGC GGC AAC AGC AGC GAG GGA GAA CTC TCG   336
         34   Asn Gly Gly Gly Gly Gly Asn Ser Ser Glu Gly Glu Leu Ser

CCC TCT CCG CCC CCG ACC CCC GCG CCC GCC TCG CCC GAG GCG   378
         48   Pro Ser Pro Pro Pro Thr Pro Ala Pro Ala Ser Pro Glu Ala

GGC GCG GTC TCG ACG CCC CCG GTC CCG CCG CCC TCG GTC TCG   420
         62   Gly Ala Val Ser Thr Pro Pro Val Pro Pro Pro Ser Val Ser

CGC AGG AAG CCC CCG CGG AAC AAC AAC CGG ACG CGC GTC CAC   462
         76   Arg Arg Lys Pro Pro Arg Asn Asn Asn Arg Thr Arg Val His

GGC GAC AAG GCC ACC GCG CAC GGG CGC AAG CGC ATC GTG TGC   504
         90   Gly Asp Lys Ala Thr Ala His Gly Arg Lys Arg Ile Val Cys

CGG GAG CGG CTG TTC TCG GCG CGG GTG GGG GAC GCG GTC AGC   546
        104   Arg Glu Arg Leu Phe Ser Ala Arg Val Gly Asp Ala Val Ser

TTC GGG TGC GCC GTC TTC CCG CGC GCC GGG GAG ACC TTC GAG   588
        118   Phe Gly Cys Ala Val Phe Pro Arg Ala Gly Glu Thr Phe Glu

GTC CGC TTC TAC CGC CGC GGG CGC TTC CGC TCG CCC GAC GCC   630
        132   Val Arg Phe Tyr Arg Arg Gly Arg Phe Arg Ser Pro Asp Ala

GAC CCC GAG TAC TTT GAC GAG CCC CCG CGC CCG GAG CTC CCG   672
        146   Asp Pro Glu Tyr Phe Asp Glu Pro Pro Arg Pro Glu Leu Pro

CGG GAG CGG CTC CTC TTC AGC TCC GCC AAC GCC TCC CTC GCC   714
        160   Arg Glu Arg Leu Leu Phe Ser Ser Ala Asn Ala Ser Leu Ala

CAC GCG GAC GCG CTC GCG CCC GTC GTC GTC GAG GGC GAG CGC   756
        174   His Ala Asp Ala Leu Ala Pro Val Val Val Glu Gly Glu Arg

GCG ACC GTC GCC AAC GTC TCG GGC GAG GTG TCC GTG CGC GTG   798
        188   Ala Thr Val Ala Asn Val Ser Gly Glu Val Ser Val Arg Val

GCC GCG GCG GAC GCC GAG ACC GAG GGC GTC TAC ACG TGG CGC   840
        202   Ala Ala Ala Asp Ala Glu Thr Glu Gly Val Tyr Thr Trp Arg
```

FIG. 2 (cont.)

```
        GTG CTG TCC GCC AAC GGC ACC GAG GTC CGG AGC GCC AAC GTC  882
    216 Val Leu Ser Ala Asn Gly Thr Glu Val Arg Ser Ala Asn Val

TCG CTC CTC CTG TAC AGC CAG CCC GAG TTC GGC CTG AGC GCG  924
    230 Ser Leu Leu Leu Tyr Ser Gln Pro Glu Phe Gly Leu Ser Ala

CCG CCC GTC CTC TTC GGT GAG CCC TTC CGG GCG GTG TGC GTC  968
    244 Pro Pro Val Leu Phe Gly Glu Pro Phe Arg Ala Val Cys Val

GTC CGC GAC TAC TAC CCG CGG CGC AGC GTG CGC CTG CGC TGG 1008
    258 Val Arg Asp Tyr Tyr Pro Arg Arg Ser Val Arg Leu Arg Trp

TTC GCG GAC GAG CAC CCG GTG GAC GCC GCC TTC GTG ACC AAC 1050
    272 Phe Ala Asp Glu His Pro Val Asp Ala Ala Phe Val Thr Asn

AGC ACC GTG GCC GAC GAG CTC GGG CGC CGC ACG CGC GTC TCC 1092
    286 Ser Thr Val Ala Asp Glu Leu Gly Arg Arg Thr Arg Val Ser

GTG GTG AAC GTG ACG CGC GCG GAC GTC CCG GGC CTC GCG GCC 1134
    300 Val Val Asn Val Thr Arg Ala Asp Val Pro Gly Leu Ala Ala

GCG GAC GCC GCG GAC GCG CTC GCG CCG AGC CTG CGC TGC GAG 1176
    314 Ala Asp Ala Ala Asp Ala Leu Ala Pro Ser Leu Arg Cys Glu

GCC GTG TGG TAC CGC GAC AGC GTG GCC TCG CAG CGC TTC TCC 1218
    328 Ala Val Trp Tyr Arg Asp Ser Val Ala Ser Gln Arg Phe Ser

GAG GCC CTG CGC CCC CAC GTC TAC CAC CCG GCG GCG GTC TCG 1260
    342 Glu Ala Leu Arg Pro His Val Tyr His Pro Ala Ala Val Ser

GTG CGC TTC GTC GAG GGC TTC GCC GTC TGC GAC GGC CTC TGC 1302
    356 Val Arg Phe Val Glu Gly Phe Ala Val Cys Asp Gly Leu Cys

GTG CCC CCG GAG GCG CGC CTC GCC TGG TCC GAC CAC GCC GCC 1344
    370 Val Pro Pro Glu Ala Arg Leu Ala Trp Ser Asp His Ala Ala

GAC ACC GTC TAC CAC CTC GGC GCC TGC GCG GAG CAC CCC GGC 1386
    384 Asp Thr Val Tyr His Leu Gly Ala Cys Ala Glu His Pro Gly

CTG CTC AAC GTG CGG AGC GCC CGC CCG CTG TCG GAC CTC GAC 1428
    398 Leu Leu Asn Val Arg Ser Ala Arg Pro Leu Ser Asp Leu Asp

GGG CCC GTC GAC TAC ACC TGC CGC CTC GAG GGC CTG CCC TCG 1470
    412 Gly Pro Val Asp Tyr Thr Cys Arg Leu Glu Gly Leu Pro Ser

CAG CTG CCC GTC TTC GAG GAC ACG CAG CGC TAC GAC GCC TCC 1512
    426 Gln Leu Pro Val Phe Glu Asp Thr Gln Arg Tyr Asp Ala Ser

CCC GCG TCC GTG AGC TGG CCC GTC GTG AGC AGC ATG ATC GTC 1554
    440 Pro Ala Ser Val Ser Trp Pro Val Val Ser Ser MET Ile Val

GTC ATC GCC GGC ATC GGG ATC CTG GCC ATC GTG CTG GTC ATC 1596
```

F I G. 2(cont.)

454 Val Ile Ala Gly Ile Gly Ile Leu Ala Ile Val Leu Val Ile

ATG GCG ACG TGC GTC TAC TAC CGC CAG GCG GGG CCG TGA CGT 1638
468 MET Ala Thr Cys Val Tyr Tyr Arg Gln Ala Gly Pro TER

CCC GCG CGT CCC CCC CCA CGT CGA ATC AAT AAA CGA CAG CGA 1680

GTC CGA CCC GCG CCC TCG CGC TTG TGT GTG TCG CGC GCG CCC 1722

FIG.4
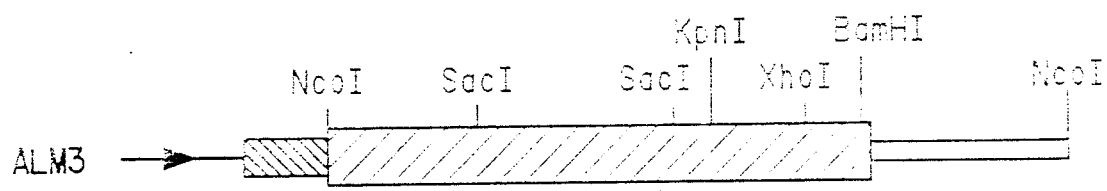
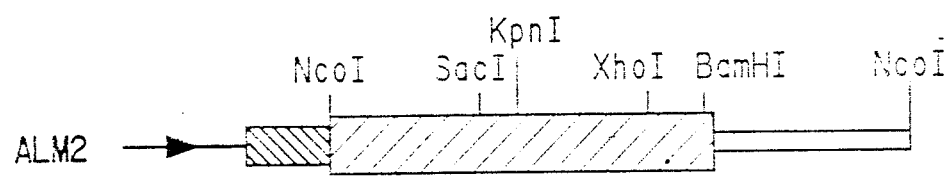
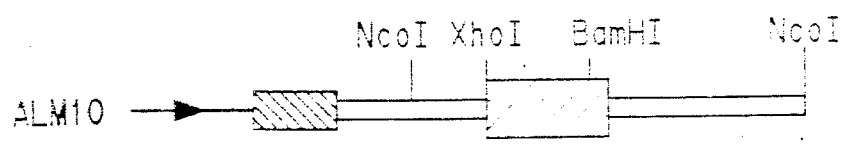

FIG. 9
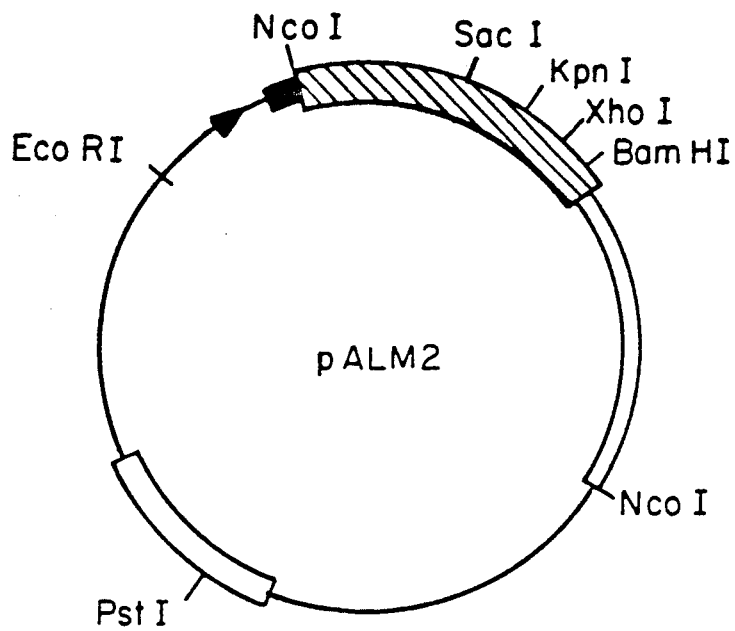
CUT WITH EcoRI
FILLED IN WITH KLENOW + NTP'S
RE-LIGATED
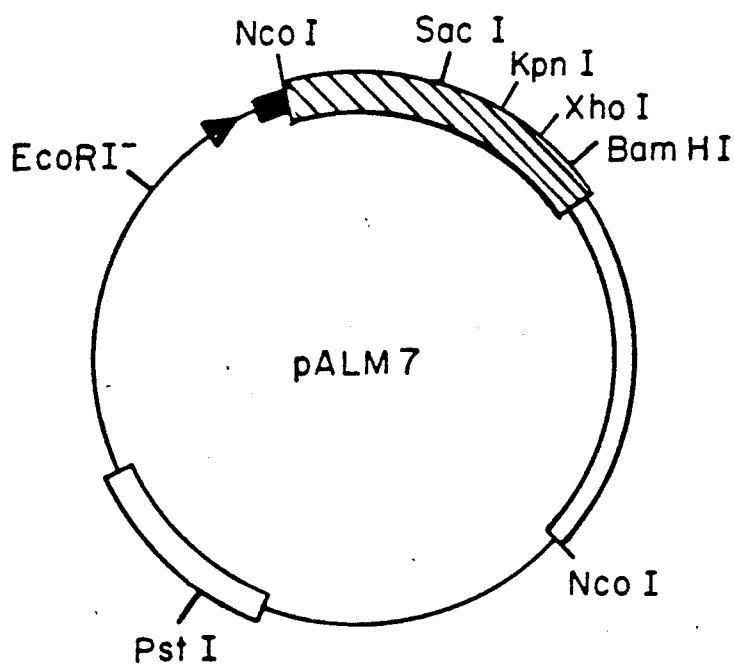

FIG. 13
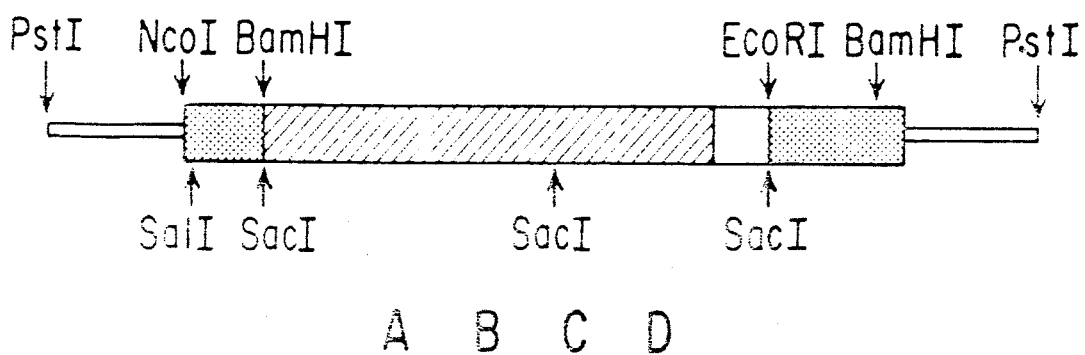
A B C D
7.3 kb →
4.3 kb →
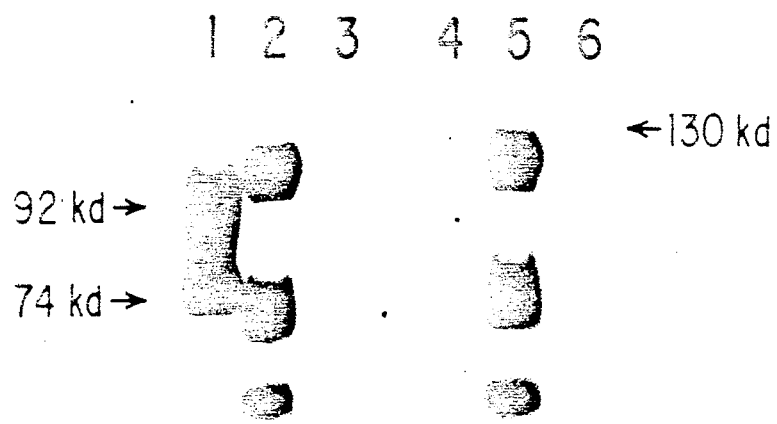
1 2 3 4 5 6
← 130 kd
92 kd →
74 kd →

FIG. 14
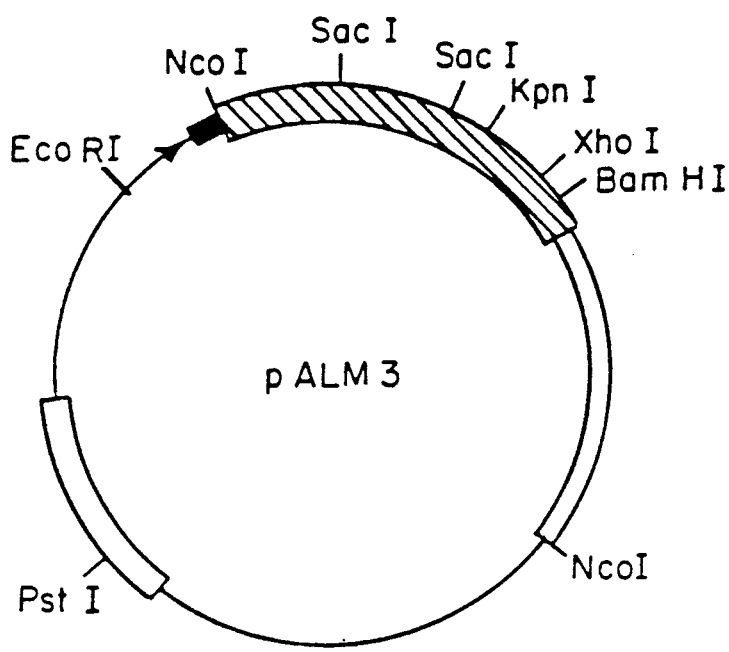
CUT WITH EcoRI
FILLED-IN WITH KLENOW + NTP'S
RE-LIGATED
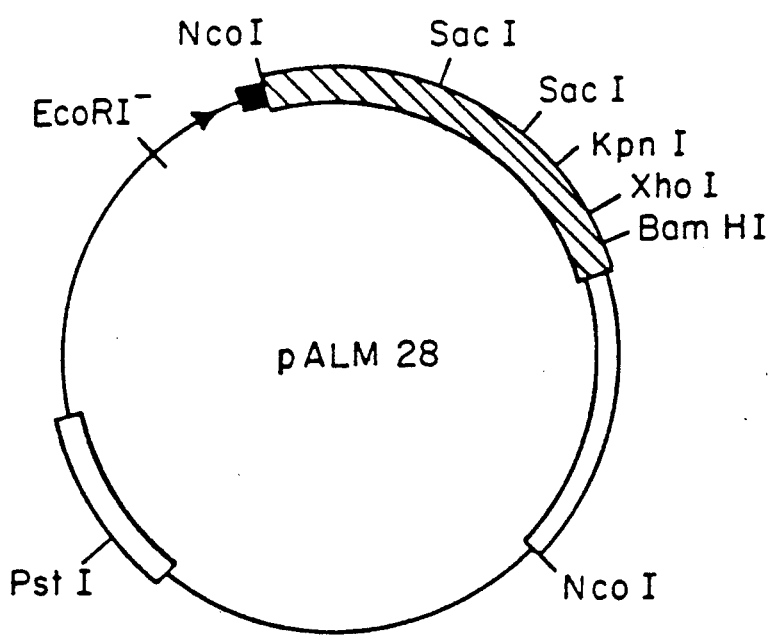

PSEUDORABIES VIRUS RECOMBINANTS AND THEIR USE IN THE PRODUCTION OF PROTEINS

BACKGROUND OF THE INVENTION

1. Field of the Invention

The present invention concerns novel Pseudorabies virus recombinants and the use of such recombinants in the production of desired proteins.

2. State of the Art

Developments in genetic engineering have made it possible to isolate DNA fragments containing specific genes or portions thereof from the genome of one organism or microorganism and insert those fragments into another DNA molecule called a vector. The recombinant construct thus created is then introduced into a host such as a bacterial, yeast, insect or animal cell, where it is propagated and, if desired, the protein encoded by the fragment insert produced. The genetic information required for the recombinant construct's propagation in the host is generally provided by the vector molecule.

Because of problems inherent in the use of large scale animal and insect cell cultures, much of the effort in this area has been directed to utilizing bacteria and yeasts as host organisms. However recent advances in cell culture techniques have made the use of large scale cultures a feasible means to produce commercially important proteins. Animal and insect cells offer sophisticated protein processing capabilities such as glycosylation, methylation, phosphorylation and sugar and lipid association which are often unavailable in bacterial or yeast systems. Since many proteins products must be glycosylated or otherwise processed for activity, recombinants capable of propagation and expression in such hosts yield enormous promise for the production of a variety of enzymes, hormones, antigens, antibodies and other proteins having medical, agricultural or industrial utility. Viruses, with their ability to infect, replicate and express proteins in animal and insect cells as well as other hosts, provide a starting point for the creation of recombinants directed to these ends. Viruses engineered to contain foreign genes coding for antigens could also be employed as live vaccines.

European patent application 0,073,656 dated Aug. 26, 1982 discusses, inter alia, the production of hepatitis surface antigen in vertebrate cell cultures tranformed with recombinant DNA constructed using a simian virus 40 (SV40) with an excised VP-1 gene, *E. coli* plasmid pBR322, and the gene encoding the surface antigen of hepatitis B virus, HBsAg. SV40 is a small DNA virus infecting some strains of monkeys. It is not known to be pathogenic for humans but has been found to cause tumors in animals.

The construction of hybrid vaccinia viruses by genetic engineering to produce live vaccines is described by Smith et al., Proc. Natl. Acad. Sci. USA, 80:7155-7159, (1983). The authors discuss the insertion and expression of the influenza virus hemagglutinin gene in vaccinia virus, a virus with a large DNA genome. The foreign gene was inserted into the thymidine kinase gene because that gene is nonessential for viral replication and simultaneously provided a selective process for recombinant viruses. Cells infected with the engineered vaccinia virus produced glycosylated hemagglutinins and the virus successfully immunized hamsters against infection with influenza virus. The vaccinia virus can be grown in the cells of numerous animal and avian species. However, a general concern with vaccinia virus is that it is infectious for humans and has been known to cause disease.

Roizman et al., Science 229: 1208-1214 (1985) points out that one of the central objectives of studies on the molecular biology of viruses infecting humans and animals is the specific modification of the viral genomes for use as vaccines or as vectors of genes whose products provide protection against infectious disease. They describe strategies to engineer another large DNA virus, herpes simplex virus type 1 (HSV-1), a human pathogen, and note the problems inherent in using large DNA viruses as vectors for foreign DNA. Shih et al., Proc. Natl. Acad. Sci. USA, 81: 5867-5870, (1984), describe a HSV-1 engineered to cause infected cells to produce and excrete the Hepatitis B virus surface antigen. HSV-1 is a common human pathogen that establishes itself in the latent state often resulting in a recurring infection—cold sores. The latent state and recurrence of infections persists for the rest of the life of the infected person.

While it has been established that the DNA of SV40, HSV-1, vaccinia and a few others can be used as vectors for the introduction and expression of foreign genes in cellular environments, there is no question that the development of other viral vectors having similar capabilities but lacking the liabilities of many of those currently employed would be of great importance to the medical, agricultural and industrial community.

U.S. Pat. No. 4,514,497 discloses the use of the pseudorabies virus as a vaccine for pigs. Pseudorabies is a large DNA virus and is a known pathogen for swine, causing the syndrome known as Aujusky's disease. To be used as a vaccine, the virus was attenuated by excising or altering its thymidine kinase gene. No additional genes were added to the virus and it vaccinated the pigs only against pseudorabies.

SUMMARY OF THE INVENTION

The present invention shows that the swine herpesvirus, pseudorabies virus, which has no record as a human pathogen but which has a wide host range, can be used as a vector for the introduction and expression of foreign genes in cells. The invention comprises all essential portions of the pseudorabies virus genome and optionally includes foreign gene inserts and generated EcoRI sites. The engineering of pseudorabies virus DNA to produce recombinant viruses is described. Particular focus is placed on manipulation of a nonessential region of the viral genome which begins at the first XhoI restriction enzyme cleavage site immediately upstream from a gIII glycoprotein gene and ends after the last base pair of that gene (hereinafter referred to as the "XhoI/gIII region"), a region heretofore not known to be nonessential to viral infectivity and replication. Portions of this region can be deleted, and alternatively or in addition, foreign genes can be inserted and expressed. Moreover, since the gIII gene contained within this region codes for a protein which is subsequently glycosylated in the cell, this region, and in particular the gIII gene located therein, presents possibilities for the insertion of foreign genes and the cellular processing, particularly glycosylation, of proteins produced thereby. The employment of the recombinants of the invention for the production of desired proteins such as enzymes, hormones, antigens and antibodies having medical, agricultural and industrial utility is also detailed. Antigenic proteins produced by the described process should be useful in diagnostic kits and as vaccine agents. In addition, the pseudorabies virus engineered to contain the genes for appropriate antigens also should have utility as a live vaccine. Finally, a further aspect of the invention involves the creation of unique EcoRI restriction enzyme cleavage sites in the pseudorabies virus genome, resulting in a large viral DNA vector capable of easy manipulation.

In its specific aspects, the present invention involves a recombinant pseudorabies virus comprising: a pseudorabies virus genome optionally having at least a portion of at least one nonessential region deleted therefrom; and a foreign DNA fragment coding for a desired protein and capable of being expressed, wherein the foreign DNA fragment is inserted in the pseudorabies virus genome at a point selected from within a nonessential XhoI/gIII region of the genome. Preferably, the foreign DNA fragment is inserted into the gIII gene segment of the XhoI/gIII region. Most preferably, it is inserted into this segment downstream from a remaining ATG codon located in the gene. Deletions may be made in any nonessential region. Prefered are deletions in the XhoI/gIII region, the tk gene region and the gI gene region. Most preferably, the deleted portion of the XhoI/gIII region is selected from within the gIII segment of the region.

The invention also concerns a recombinant pseudorabies virus comprising a pseudorabies virus genome having at least a portion of a nonessential XhoI/gIII region of the genome deleted therefrom and optionally having at least a portion of at least one other nonessential region deleted therefrom. Preferably the deleted portion of the XhoI/gIII region is selected from within the gIII gene segment of the region. Other nonessential regions from which deletions can be made are preferably the tk gene region and the gI gene region.

In addition, the present invention involves a recombinant pseudorabies virus comprising: a pseudorabies virus genome optionally having at least a portion of at least one nonessential region deleted therefrom; and an EcoRI site generated in a remaining nonessential region of the pseudorabies virus genome. Preferably, the EcoRI site is generated at a point selected from within the XhoI/gIII region. More preferably, it is generated at a point selected from within the gIII gene segment of the XhoI/gIII region. Most preferably, it is generated at a point selected from within the gIII gene segment, downstream from a remaining ATG codon. Deletions may be made in any region that is nonessential. Prefered are deletions in the XhoI/gIII region, the tk gene region and the gI region. Most preferably the deleted portion of the XhoI/gIII region is selected from within the gIII gene segment of the region.

Finally, the invention contemplates a process for producing a protein comprising: (1) infecting cells with recombinant pseudorabies virus containing a foreign DNA fragment coding for a desired protein and capable of being expressed; (2) culturing the infected cells until the desired protein is produced; and (3) recovering the protein. The invention also encompasses those proteins produced by this process.

BRIEF DESCRIPTION OF THE DRAWINGS

Unless otherwise indicated, the Figures are not shown to scale. FIG. 1 shows maps of the pseudorabies virus (PRV) genome indicating the DNA restriction fragments used to study the gIII glycoprotein gene. (A) The genome of PRV depicting the unique long ($U_L$) and unique ($U_S$) regions and the inverted terminal repeat sequences bracketing $U_S$ ($IR_S$ and $TR_S$, respectively). The genome is divided into map units for reference as indicated. (B) The BamHI restriction enzyme cleavage map of the PRV genome. The gIII gene is located within the two adjacent BamHI fragments, BamHI-2 and BamHI-9. A 4.3 kb PstI fragment containing the gIII gene is expanded in (B) and detailed in (C) with a number of restriction enzyme cleavage sites noted. In (C), the shaded box corresponds to the gIII glycoprotein gene, the sequence of which is given in FIG. 2. The mRNA transcript for this gene and its orientation is indicated by the arrow.

FIG. 2 provides the complete nucleotide sequence of the gIII gene (noncoding strand). The DNA sequence for 196 bp upstream and 90 bp downstream from the gene is also given. The numbers at the right of the sequence designate nucleotide numbers. The corresponding amino acids are given below each codon using the conventional three-letter code, and are numbered at the left.

FIG. 3 show representations of a number of plasmids and the routes to constructing (A) pALM2 (B) pALM10 and (C) pALM15. The plasmid molecules are drawn as circles with relevant elements and sites indicated. All plasmids are *E. coli* pBR322 derivatives. Each plasmid has a unique PstI site located within the B-lactamase gene (open box) derived from pBR322. The black arrow denotes the tac promoter/operator region followed by DNA encoding the amino terminal 23 amino acids of the bacteriophage Lambda Cro gene (black box). The shaded box represents the PRV gIII glycoprotein gene with relevant restriction enzyme sites indicated. The ATG codon in the NcoI site at the junction of Cro and gIII defines the first amino acid of the gIII. A double line immediately following and/or preceding the gIII gene indicates contiguous PRV DNA sequences downstream or upstream of the gIII gene. DNA fragments removed or ligated together for plasmid construction are indicated as barred lines above the plasmid map. Construction details of each plasmid are outlined under the Detailed Description of the Invention.

FIG. 4 represents the patterns of proteins after electrophoresis on SDS polyacrylamide gels. Lane 1 represents the proteins from an uninduced culture of bacteria carrying plasmid pALM3. Lanes 2, 3 and 4 represent the proteins obtained from induced cultures of bacteria carrying plasmids pALM3, pALM2 and pALM10, respectively.

FIG. 5 shows a Southern blot analysis of virion DNA extracted from parental PRV, PRV-2 and PRV-10. Lanes 1, 2 and 3 contain the DNA from parental PRV, PRV-2 and PRV-10, respectively. The figure also contains a restriction map of the 4.3 kb PstI PRV fragment. The gIII gene is indicated by the shaded rectangle. The mRNA and the direction of transcription are designated by an arrow below the line. The 3.6 kb SphI-NcoI DNA fragment carried by pALM15 used as a probe is shown below the map.

FIG. 6 shows gene maps as follows: (A) genomic arrangement of HTLVIII DNA; (B) HTLVIII envelope polyprotein gene (env gene) region indicating the processing site (black inverted triangle) of the env gene products; (C) restriction map of the env gene coding region; (D) BglII 1.43 kb HTLVIII DNA fragment (from env coding region) with kinased SacI/BglII linker; (E) pseudorabies virus DNA portion of pALM2 expression vector showing the point of insertion of the HTLVIII-linker DNA fragment of part (D) in the construction of pALM24.

FIG. 7 shows the pattern of proteins on SDS polyacrylamide gels resulting from the electrophoresis of immunoprecipitated extracts of cells infected with the following: lanes 7, 8 and 9, parental PRV; lanes 1, 2 and 3, PRV-2; lanes 4, 5 and 6, PRV-24. Lanes 1, 4 and 7 were reacted with antisera raised against the protein produced by a BglII to BamHI fragment of the HTLVIII gene from bp 7198 to 8052, as described in Ratner et al., Nature, 313:277–284 (1985). Lanes 2, 5 and 8 were reacted with serum 490. Lanes 3, 6 and 9 were reacted with M2 monoclonal antibody. Lane M denotes molecular weight standards.

FIG. 8 shows the pattern of DNA resulting from the electrophoresis of PstI fragments of DNA on a 1% agarose/TEA gel followed by hybridization with either a gIII specific probe (lanes 1, 2 and 3) obtained from pALM 15 or an HTLVIII envelope specific probe, a KpnI fragment of the HTLVIII gene from bp 5928 to 8596 (lanes 4, 5 and 6). Lane M denotes molecular weight standards. Lanes 1 and 4 contain DNA from parental PRV. Lanes 2 and 5 contain DNA from PRV-2. Lanes 3 and 6 contain DNA from PRV-24.

FIG. 9 shows the construction of plasmid pALM7 from pALM2.

FIG. 13 (top) shows a linear representation of the gIII-lacZ fusion present in PRV-Z1. The center figure shows the pattern of DNA resulting from the electrophoresis of PstI fragments of DNA on a 1% agarose/TEA gel followed by hybridization with a parental DNA specific probe obtained from pALM15 or a lacZ probe obtained from pMLB1034. The DNA in lanes A and C came from parental (unaltered) virus while that in lanes B and D came from PRV-Z1. Lanes A and B were hybridized with gIII DNA from pALM15 while lanes C and D were hybridized to the lacZ probe. The bottom figure shows the pattern of proteins on polyacrylamide SDS gels resulting from the electrophoresis of immunoprecipitated extracts of cells infected with: lanes 1, 2 and 3 parental PRV; lanes 4, 5 and 6, PRV-1. Lanes 1 and 4 were precipitated with antiserum 490. Lanes 2 and 5 were precipitated with M2 monoclonal antibody. Lanes 3 and 6 were precipitated with antibody to betagalactosidase of E. coli.

FIG. 14 shows the construction of plasmid pALM28 from pALM3.

DETAILED DESCRIPTION OF THE INVENTION

The various aspects of the invention involve pseudorabies virus (PRV) having deletions and/or insertions in the nonessential regions of viral genome. PRV without alterations in the genome is refered to throughout as either parental or unaltered PRV. PRV with alterations in the genome is termed recombinant PRV. Of particular interest are PRV with deletions and/or insertions in a nonessential region of the genome which begins with a first XhoI restriction enzyme cleavage site immediately upstream from the pseudorabies gIII glycoprotein gene (hereinafter referred to as the "first XhoI restriction enzyme cleavage site") and ends after the final base pair of that gene, referred to hereinafter as the "XhoI/gIII region". As used herein, "upstream" is defined as being on the 5' side of the mRNA of any given gene. "Downstream" is on the 3' side of the mRNA of any given gene.

The specific PRV strain employed as a starting material in the present invention is not critical, as long as it contains a gIII gene region. Examples of suitable strains include the Becker strain, the Ka strain and the Bartha strain, described in Robbins et al. J. Virol., 58: 339–347 (1986) (Becker); Ben Porat et al., J. Virol., 57: 191–196 (1986) (Ka and Bartha); and Lomniczi et al., J. Virol., 52: 198–205 (1984) (Ka and Bartha). The Becker strain is the preferred strain employed in the present invention.

Figure 1:
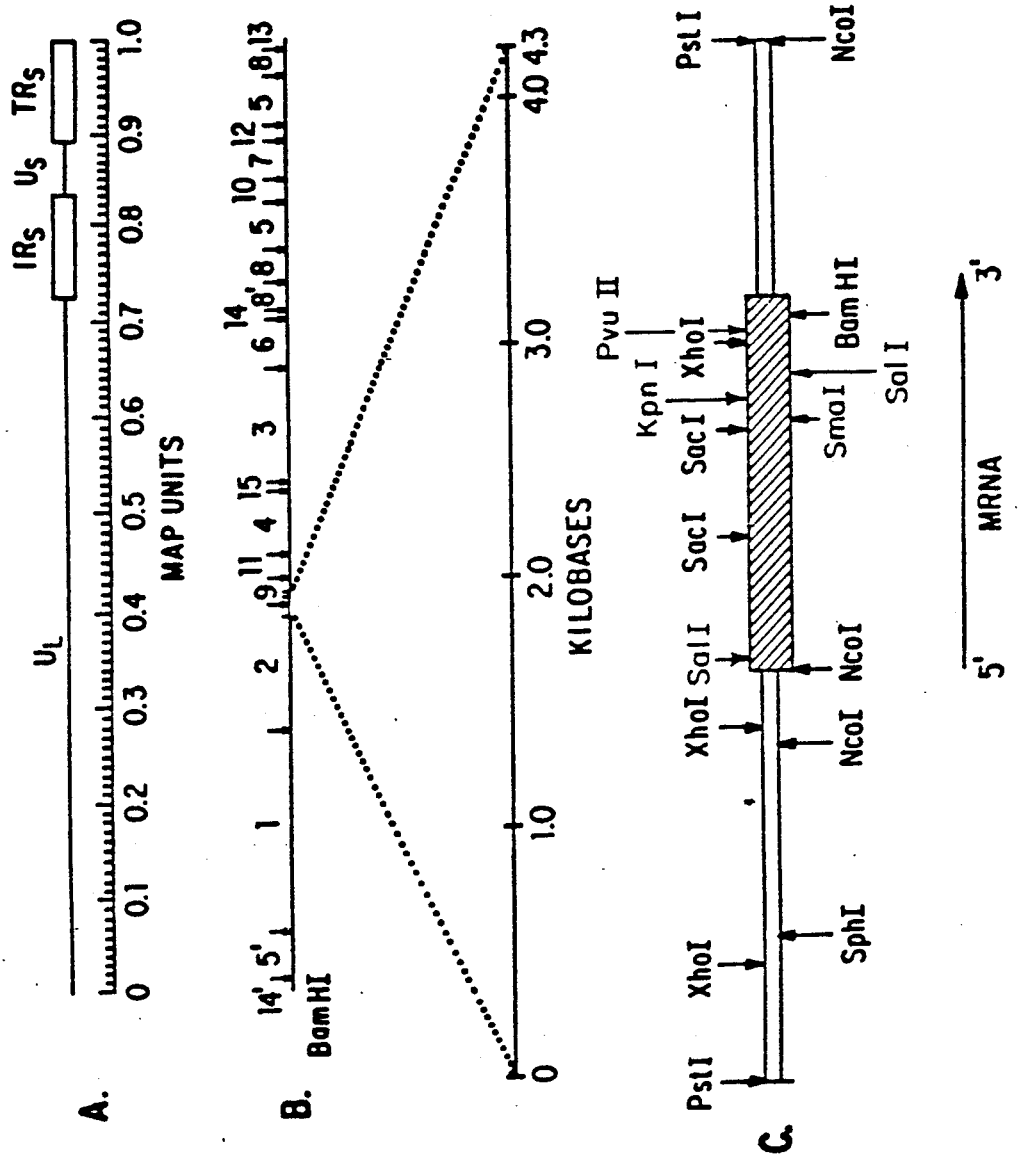

The XhoI/gIII region is located at approximately 0.4 on the PRV genome within a 4.3 kb PstI fragment (FIG. 1). The gIII gene contained within this region is a structural gene which codes for a PRV envelope glycoprotein. The complete base pair sequence of the gIII gene (noncoding strand) is given in FIG. 2. The DNA sequence for 196 bp upstream and 90 bp downstream from the gene is also given in FIG. 2.

The XhoI/gIII region, and any other nonessential region of the PRV genome, car be manipulated to produce the deletions and insertions required in the invention by using standard recombinant DNA techniques known in the art such as those described in Maniatis et al., Molecular Cloning, A Laboratory Manual, Cold Spring Harbor Laboratory, Cold Spring Harbor, N.Y. (1982); Myers et al., Science, 229: 242–247 (1985); Botstein et al., Science, 229: 1193–1201 (1985); Roizman et al., Science, 229: 1208–1214 (1985); and Graham et al., Virology, 52: 456–467 (1973). In general terms, the procedure would involve cleavage of the PRV genome using one or more restriction enzymes to produce genomic fragments, followed by isolation of the fragment containing the region which is to be the subject of the manipulation. This fragment could then be cloned into a vector. Any bacterial plasmid or bacteriophage vector could be utilized provided it contains a selectable marker. Suitable plasmid and bacteriophage vectors include, but are not limited to, E. coli plasmid pBR322, E. coli pSC101, bacteriophage λ, and bacteriophage M13. Other vector systems, including yeast, can also be used. Preferred for ease of manipulation is E. coli plasmid pBR322.

Utilizing the plasmid or bacteriophage vectors cloned with a PRV DNA fragment, deletions within the PRV fragment could be effected by conventional techniques employing endonucleases, exonucleases and the like. Insertions, if desired, could also be made using techniques known to those skilled in the art. A plasmid available for such use is the plasmid pALM20 carried by E. coli strain NF1829, on deposit with the American Type Culture Collection in Rockville, Md. bearing the accession number ATCC No. 67151. This plasmid is an Amp$^S$, Tet$^R$, pBR322 plasmid having cloned at the PstI site a 4.3 kb PstI PRV fragment containing the gIII gene (shown in FIG. 1) taken from the Becker strain of PRV.

The plasmid or bacteriophage DNA having the desired manipulations can then be selected for using conventional methods, and introduced for propagation purposes into a host cell or organism using standard transformation procedures. Any host cell or organism in which the plasmid or bacteriophage can be propagated could be utilized. For example, in the case of a manipulated pALM20, the host organism would be *E. coli.*

To produce recombinant PRV containing the deletions and insertions effected in the PRV fragment in the plasmid, standard cotransfection procedures could be employed. Specifically, the plasmid or bacteriophage could be isolated from the host organism, mixed with unaltered PRV DNA and cotransfected into host cells. The plasmid or the bacteriophage and the PRV DNA would enter the cells where homologous recombination would take place, resulting in the replacement of the unaltered region in the viral DNA with the corresponding altered region from the plasmid or bacteriophage DNA. To increase the efficiency of cotransfection and homologous recombination, the plasmid or bacteriophage DNA may be linearized prior to mixing with the unaltered PRV DNA. Any host cell suitable for plasmid or bacteriophage and PRV DNA transfection and subsequent recombinant virus propogation can be utilized in this procedure. The recombinant PRV DNA is then replicated within the cell and the viruses which have undergone the desired recombination could be selected for using standard techniques.

In one aspect, the present invention involves PRV engineered to carry foreign DNA fragments coding for a desired protein and capable of being expressed. The foreign fragment is inserted in the PRV genome at a point selected from within the nonessential XhoI/gIII region of the genome. Preferably, insertions are made into the gIII gene segment of the XhoI/gIII region. Most preferably, insertions are made into this segment downstream from a remaining ATG codon sequence. The positions of the ATG codons in the gIII gene are illustrated in FIG. 2. By gIII gene segment it is meant the gIII glycoprotein coding sequence.

The present invention in all of its embodiments requires that all essential regions of the PRV genome be present. However, nonessential regions within the genome may, but need not, be deleted in whole or in part in all embodiments. As used herein, an "essential region" is any region of the PRV genome, the deletion of which would result in a complete cessation of viral propagation. As used herein propagation encompasses viral infectivity replication and release. Cessation of viral propogation has occurred where the virus is unable to propagate even with the assistance of a helper virus or a complementing cell line. "Helper viruses" are replication competent infectious viruses that provide gene products required for the propagation of coinfecting defective viruses that, by definition, cannot propagate themselves. Such viruses are described in Topley & Wilson's Principles of Bacteriology, Virology and Immunity, Vol. 4 (Virology), F. Brown and G.S. Wilson, eds., G.S. Wilson, A.A. Miles and M.T. Parker, series eds. (Williams and Wilkins, Baltimore, Md. 1984), and are well known to those skilled in virology. Examples of helper viruses suitable for use in the present invention include unaltered PRV as well as other viruses that express the genes contained within the deleted region whose products are necessary for propagation of the recombinant PRV. "Complementing cell lines" are cell lines that provide gene products required for the propagation of defective viruses that, by definition, cannot propagate themselves. Thus, a "nonessential region", as that phrase is defined herein, is any region, the deletion of which would not result in a complete cessation of viral propagation. Cessation of viral propagation has not occurred where the virus is able to propagate, with or without the assistance of a helper virus. It is believed that approximately 40% of the viral genome is nonessential.

Preferably, deletions are made in nonessential regions of the PRV genome such as the XhoI/gIII region, the tk gene region, as described in U.S. Pat. No. 4,514,497, and the gI gene region, as described in Ben Porat et al., J. Virol., 57: 191–196 (1986); and Mettenleiter et al., J. Virol., 53: 52–57 (1985). Deletions in the aforementioned regions are preferred because such deletions do not necessitate the use of a helper virus or a complementing cell line in order for the PRV to infect and replicate. Most preferably, the deleted portion of the XhoI/gIII region is selected from within the gIII gene segment of the region. It should be noted that the definition of the insertion region, the XhoI/gIII region, is based upon the unaltered genome having this region present. As nonessential, this region can be deleted in whole or in part, and the insertion made in the remaining portion of the region, or if entirely deleted, within the portion of the remaining genome where XhoI/gIII would have, if present, been located.

The foreign fragment insert can be any fragment which codes for a desired protein and is capable of being expressed. The maximum size of such an insert is determined by adding the cloning capacity of unaltered PRV, which is at least 3,000 and possibly 15,000 base pairs, to the number of base pairs removed in any genomic deletion. "Desired proteins" may be, but are not limited to, enzymes, hormones, antigens and antibodies. The phrase "capable of being expressed" requires that: (1) the resulting recombinant PRV DNA contain a transcription control region and a translation initiation codon sequence (ATG) upstream from the coding region of the foreign fragment; (2) the coding region of the foreign fragment be in reading frame with the translation initiation codon sequence; and (3) the desired protein produced be compatable with PRV propagation (i.e., is not lethal to the cells or the virus). The upstream translation initiation codon sequences can be supplied by either the PRV genomic portion of the recombinant virus or alternatively, by a translation initiation codon sequence insert, as desired, or as deletions and/or insertions require. FIG. 2 shows the location of the ATG codon sequences within the unaltered PRV gIII gene. Similarly, the upstream transcription control region can be supplied by either the remaining PRV genome or a transcription control region insert, again as desired or as deletions and/or insertions require. In unaltered PRV DNA, the transcription control region is located upstream from the gIII gene within a region of the PRV genome which begins with the first XhoI restriction enzyme cleavage site immediately upstream from the gIII glycoprotein gene and which ends at the first base pair of the gIII gene. Suitable transcription control region inserts include the long terminal repeat portion of the RNA tumor virus and the early or late promoter of the SV-40 virus. Such control regions are described in Experimental Manipulation of Gene Expression, M. Inouye, ed., (Academic Press 1983).

One example of a recombinant of the above embodiment is PRV-24, described below.

In another aspect, the present invention involves PRV engineered to remove all or part of the nonessential XhoI/gIII region. Within this embodiment, other nonessential regions may also, but need not, be deleted in whole or in part. The preferences as to deleted portions are as described above. Examples of this embodiment are PRV-2 and PRV-10 described below.

A further aspect provides recombinant PRV comprising a pseudorabies virus genome having generated therein an EcoRI restriction enzyme cleavage site (coding sequence 5'-GAATTC-3'), wherein the EcoRI site is located in a nonessential region of the PRV genome. Preferred are recombinants with insertions in the XhoI/gIII region, the tk gene region and the gI gene region. More preferred are recombinants with insertions in the XhoI/gIII region. Most preferably, the insertion is within the gIII gene segment of the XhoI/gIII region. The most preferred embodiment involves recombinants with insertions in the gIII gene segment downstream from an ATG codon sequence. EcoRI sites can be generated alternatively by site directed mutagenesis, or by the insertion of synthetic or naturally occurring foreign DNA fragments containing EcoRI sites. To use, recombinants containing this EcoRI site are cut with EcoRI restriction enzyme and, employing standard recombinant DNA techniques, the desired DNA fragment inserted. PRV-1 and PRV-32 are examples of a recombinant of this type.

The proteins of the instant invention are produced by: (1) infecting cells with recombinant PRV containing a foreign DNA fragment coding for a desired protein and capable of being expressed; (2) culturing the infected cells until the desired protein is produced; and (3) recovering the protein. For virus infection and protein production, the PRV is simply applied to the cells under standard cell culture conditions. To recover the protein, standard techniques are employed. Cell culture techniques and recovery methods are described in Maniatis et al., Molecular Cloning, A Laboratory Manual, Cold Spring Harbor Laboratory, Cold Spring Harbor, N.Y. (1982); Experimental Manipulation of Gene Expression, M. Inouye, ed., (Academic Press 1983); and Robbins et al., J. Mol. Appl. Gen. 2: 485-496 (1984). The specific host cells employed in the present invention are not critical as long as they allow replication and expression of the recombinant PRV DNA. Suitable cells include, but are not limited to, animal and insect cells. Preferred are mouse fibroblast cells, HeLa cells, rabbit kidney cells, swine kidney cells, lamb kidney cells, dog kidney cells, monkey kidney cells, chick embryo fibroblast cells, baby hamster kidney cells, human fibroblast cells, and any and all combinations thereof. Most preferred are swine kidney cells, in particular PK15, available from National Veterinary Services Laboratories, Ames, Iowa.

A pharmaceutically effective amount of the above-described live recombinant viruses containing foreign genes coding for an antigenic protein or an antigenic protein produced by such recombinants in accordance with the above-disclosed process can be employed along with a pharmaceutically acceptable carrier or diluent as a vaccine against disease in mammals. To be used as a vaccine, the antigenic protein need not be in pure form, but may if desired consist of cellular extracts containing any and all cellular parts and culture medium. The useful dosage to be administered and the mode of administration will vary depending upon the age, weight and mammal vaccinated and the type of pathogen against which vaccination is sought.

The antigenic proteins produced by such viruses can also be employed as diagnostic reagents in a pathogen detection kit. Specifically, the presence of a pathogen in samples of body fluids could be detected by contacting the protein with body fluids suspected of containing antibodies to that protein and measuring the formation of antigen-antibody complexes. Measurement of the complex formation can be accomplished using methods such as ELISA (enzyme-linked immunosorbent assay), strip radioimmunoassay or indirect immunofluorescence assay known to those skilled in the art and discussed in U.S. Pat. No. 4,520,113.

The following experiments and examples are illustrative of various aspects of the invention, but are not intended to limit the scope of the present invention. Unless otherwise noted all parts are by weight and all temperatures are given in degrees Celsius.

GENERAL PROCEDURES

Swine kidney cells, PK15, available from National Veterinary Services Laboratories, Ames, Iowa, were grown in Dulbecco's Eagle's Medium supplemented with 10% heat inactivated fetal bovine serum. The bovine serum and the Medium were obtained from GIBCO, Grand Island, N.Y. The Becker strain of PRV was used, although any strain of PRV is satisfactory. Cells, the virus and culture conditions are described by Robbins et al., J. Mol. Appl Gen. 2: 485-496 (1984).

Two monoclonal antibodies—designated M1 and M16—specific for the gIII envelope glycoprotein were obtained from Dr. T. Ben Porat, Vanderbilt University, Nashville, Tenn. Although the monoclonal antibodies were made using the Ka strain of PRV, they show essentially the same reactivity with the Becker strain of PRV and they neutralize the virus in the presence or absence of complement. They also immunoprecipitate gIII proteins from infected cells. Although M1 and M16 were utilized herein, any monoclonal antibodies raised against the gIII gene product could be employed.

The procedure used to purify the viruses was that described by Ben Porat et al., Virology, 60: 29-37 (1974). The procedure was modified in order to prepare $^3$H-qlucosamine labelled virus in that 100 $\mu$Ci/mL of $^3$H-glucosamine, obtained from New England Nuclear, Boston, Mass., was added. The techniques for making cell extracts for immunological analysis were described previously by Robbins et al., J. Mol. Appl. Gen., 2: 485-496 (1984).

The procedures to purify and analyze viral DNA are as follows. PRV DNA was purified from PRV nucleocapsids as described by Ben Porat et al., Virology, 41: 265-273 (1970). DNA so obtained was analyzed by the Southern blot method as described by Southern, E. M., J. Mol. Biol., 98: 503-517 (1975). DNA/DNA hybridizations were done at 37° C. for 16 hours in 60% formamide, 10 mM PIPES (piperazine-N,N'-bis[2-ethanesulphonic acid]) pH 6.5, 5x SSC (0.75 M sodium chloride and 0.075 M sodium citrate, pH 6.5), sonicated calf thymus DNA (100 ug/mL) and 5x Denhardt's solution (0.1% each of ficoll 400 [Pharmacia Inc., Piscataway, N.J.], bovine serum albumin and polyvinylpyrollidone [Sigma Chemical Company, St. Louis, Mo.]). DNA probes were prepared by nick-translation using $^{32}$P-labelled nucleotides. The hybridized nitrocellulose membranes were washed four times for 30 minutes each at 65° in 2x SSC (0.3 M sodium chloride and 0.03 M sodium citrate, pH 7.0). The nitrocellulose membrane was then prepared for autoradiography on Kodak XAR-5 film.

E. coli bacterial plasmid vectors were utilized in making the recombinant PRV DNA. They are designated by having a small p immediately preceding letters or numbers or a mixture of letters and numbers. For certain experiments, fragments of PRV DNA were inserted into an E. coli expression vector so that significant amounts of the DNA fragment and also the PRV gene product could be produced for purposes of DNA and protein analysis as well as for use in cotransfection gene replacement experiments. E. coli strain NF1829 carrying an F' plasmid with the laci$^q$ mutation which results in the overproduction of the Lac repressor was used to regulate the expression of PRV genes in the Lac expression vectors. This is important because excessive expression of the PRV gIII gene in E. coli results in growth arrest of the cells as described by Robbins et al., J. Virol. 58: 339-347 (1986).

All plasmids were constructed using standard recombinant DNA techniques as described in Maniatis et al., Molecular Cloning, A Laboratory Manual, Cold Spring Harbor Laboratory, Cold Spring Harbor, N.Y. (1982).

CONSTRUCTION OF PLASMIDS CONTAINING THE PRV gIII GENE 1. pALM20

10μg of DNA from PRV, Becker strain, and 2μg of E. coli plasmid pBR322 were separately cut with PstI and the pBR322 DNA treated with calf alkaline phosphatase for 30 minutes at 37°. The samples were fractionated on 1% agaraose/TEA gel and the linearized pBR322 and the region corresponding to approximately 4.3 kb from the PRV DNA were purified as follows using DE81 paper. First, the DE81 strips were washed in 2m NaCl, 10mm Tris pH 7.5, and 1 mm EDTA, washed twice in water and then equilibrated in TEA. The gel was cut above and below the required fragments and the DE81 strips were then placed within the cut gel and the DNA electrophoresed onto the strip. The strips into which the DNA was electophoresed were then rinsed with water and the DNA eluted off with 1.5 M NaCl, 10mm Tris pH 7.5 and 1 mm EDTA for 2 hours at 37°. The DNA was precipitated in equal volume of isopropanol at room temperature for one hour. The precipitate was collected by centrifugation. To the resulting pellets were added TEN (10 mm Tris pH 7.5, 1 mm EDTA, 100 mm NaCl). The solution was ethanol precipitated overnight at −20° and the pellets recoved by centrifugation.

100 ng of the pellet containing the linearized pBR322 isolate and 200ng of the 4.3 PRV PstI fragment were added in the presence of 1μl 10x ligase buffer, 1μl 1 mg/ml of bovine serum albumin (obtained from Sigma Chemical Company), 1 μl of ligase and H$_2$O up to 10 μl. After 3 hours at room temperature the resulting ligation mix was transformed into E. coli strain NF 1829, described above. The bacteria were then plated on Tet plates overnight at 37°. Replica plate colonies from the Tet plates were next plated on both Tet and Amp plates. Plasmid that were Tet$^R$ and Amp$^S$ were selected and analysed by Southern blot analysis. Plasmid DNAXs were then digested with PstI and EcoRI, subjected to electrophoresis on a 1% agarose/TEA gel, transferred to nitrocellulose and probed using nick-translated pALM15. A clone designated pALM20 that contained a 4.3 kb PstI fragment of PRV genomic DNA containing the gIII gene was isolated.

CONSTRUCTION OF PLASMIDS WITH DELETIONS IN THE PRV gIII GENE 1. pALM2

Figure 3A:
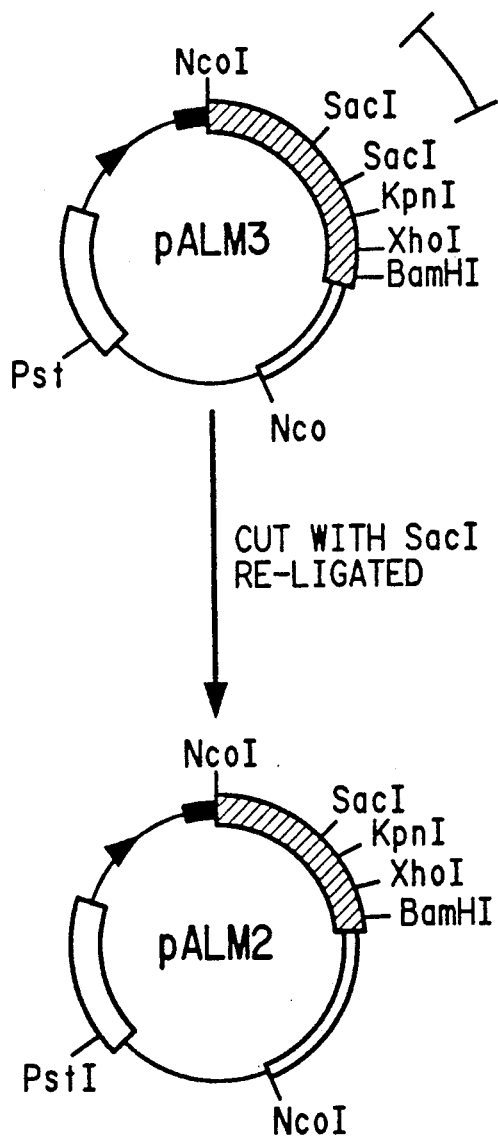

Deletions affecting gIII were constructed by altering the E. coli pBR322 derived expression plasmid pALM3 (FIG. 3A). pALM3 is described in European Patent Application 0,162,738 dated Nov. 27, 1985 (referred to therein as pNT 7/123). As noted in EPA 0,162,738, E. coli strain K12, NF1829 carrying the plasmid pALM3 (pNT7/123) is on deposit with In Vitro International, Inc., Ann Arbor, Mich., bearing the accession number IVI-10049.

In pALM3, transcription of the Cro-PRV gIII hybrid gene is directed from the tac promoter under control of the Lac repressor. E. coli strain NF1829 containing pALM3 were grown in L-broth containing 100 μg/mL of ampicillin. Fusion proteins were induced by adding isopropyl beta-D thiogalactopyranoside tô a final concentration of 1 mM. Three mL of culture was harvested 4 hours after the inducer was added. The Cro-PRVgIII fusion proteins were collected as insoluble aggregates. The proteins were fractionated by electrophoresis on a 10% SDS-polyacrylamide gel and then stained with Coomassie blue. pALM3 produces significant quantities of a CRO-PRV gIII fusion protein that accumulates to approximately 3-5% of total cell protein (FIG. 4, lane 2). As determined by DNA sequence analysis, the amino terminal 23 amino acids, derived from the bacteriophage Lambda Cro protein, are fused to the first amino acid (Met) of gIII. In pALM3, the coding sequence terminates at the natural translation stop signal (TGA) after amino acid 479 followed by approximately 1000 bp of PRV sequence.

pALM2 (FIG. 3A) was constructed by digesting pALM3 with the restriction enzyme SacI, and re-ligating. pALM2 contains an in-frame deletion of 402 bp—the internal SacI fragment—within the gIII gene and produces (as described above for pALM3) a truncated protein (FIG. 4, lane 3).

Figure 3B:
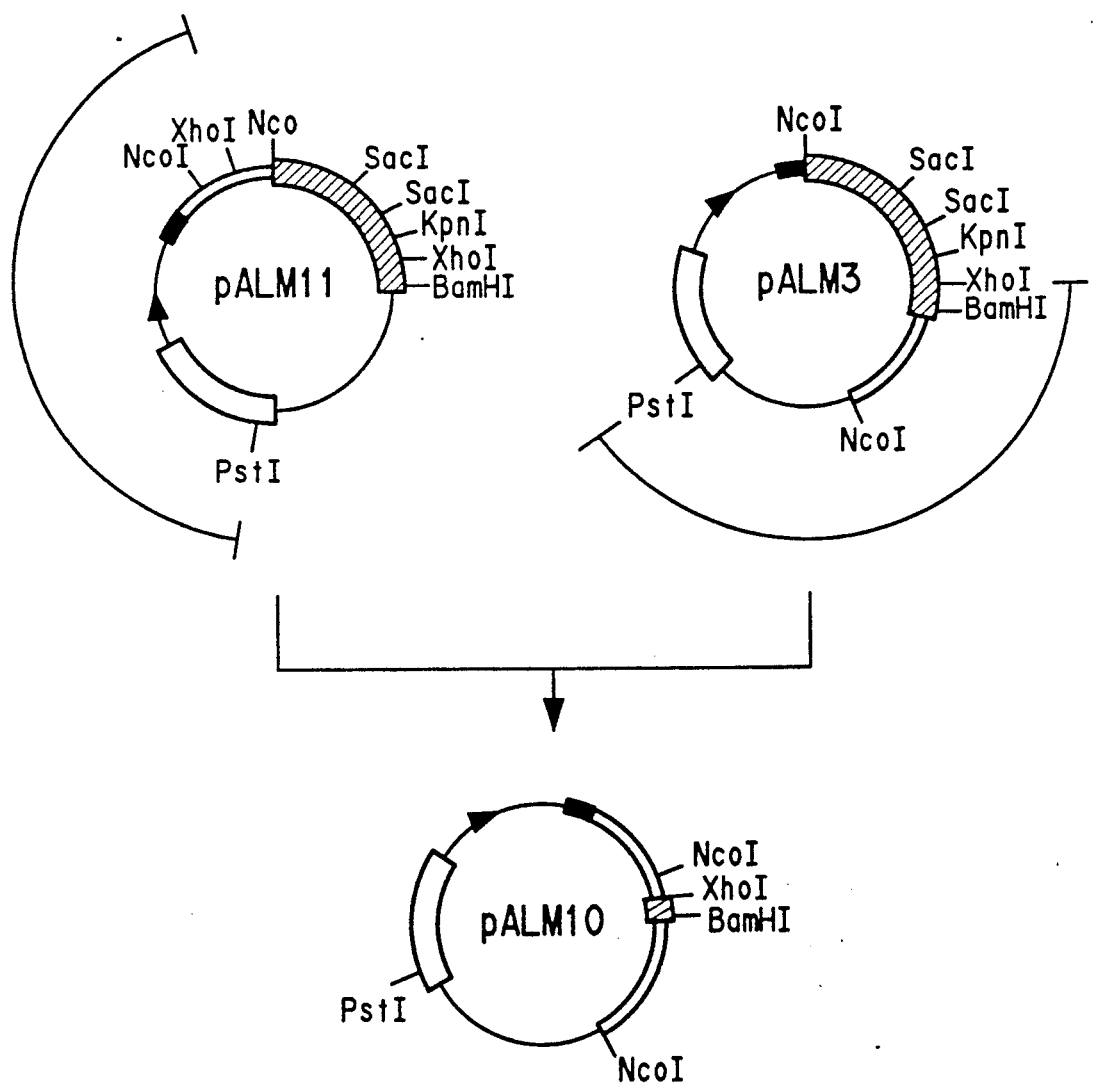
Figure 3C:
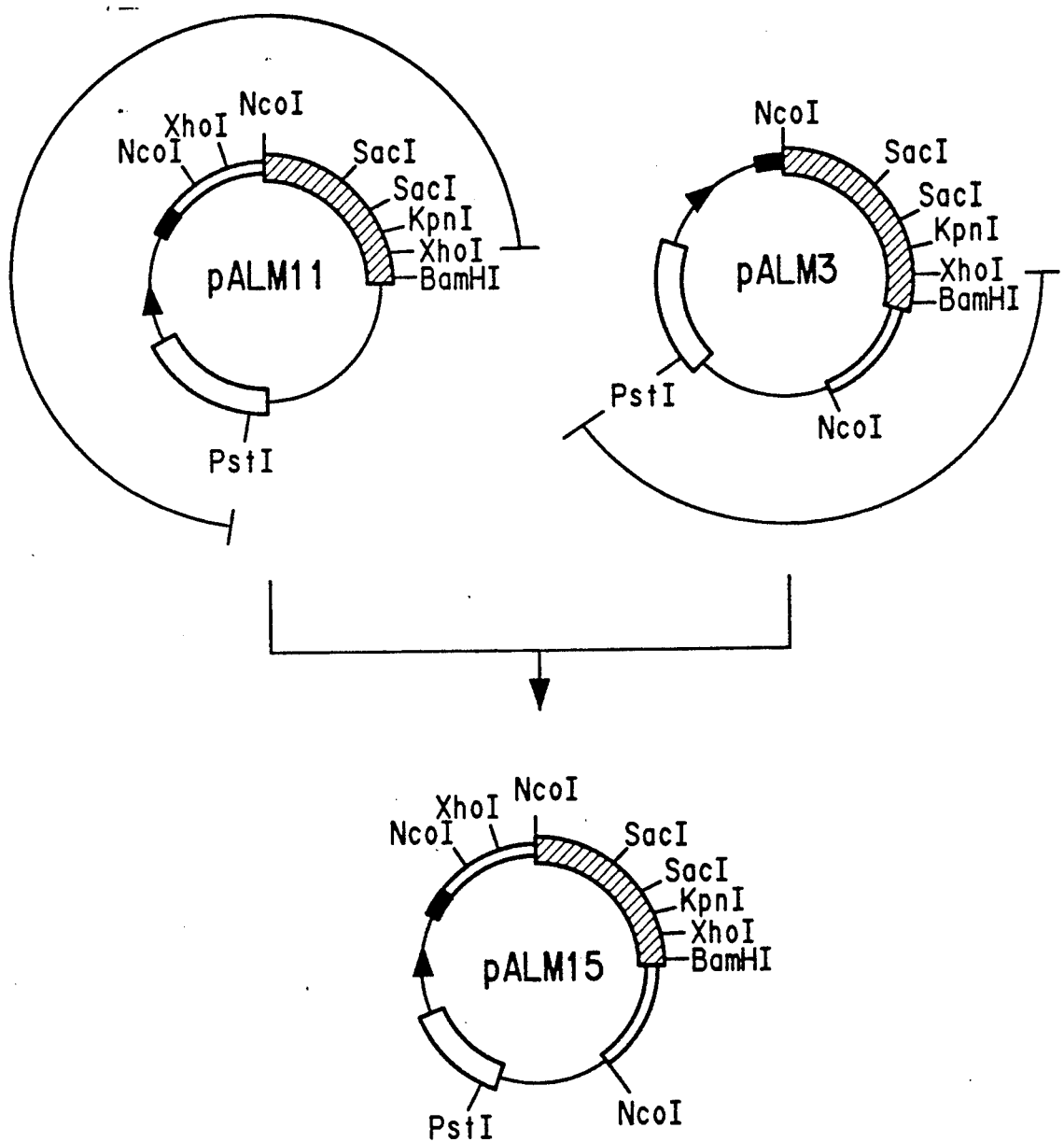

2. pALM10 pALM10 is another expression plasmid containing part of the gIII gene of PRV (FIG. 3B). In this case, about 87% of the gIII gene of PRV has been removed. It was constructed as follows. First pALM11 was constructed to serve as an intermediate. pALM11 was constructed by digesting pALM12 with SphI and removing the resulting single-stranded ends by using the 3'-5' exonuclease activity of the Klenow fragment of DNA polymerase I. The construction of pALM12, an E. coli pBR322 derivative, is described in European Patent Application 0,162,738 dated Nov. 27, 1985 (referred to therein as p7/123). The DNA was then digested with BamHI and the resulting 2500 bp fragment was ligated into the SmaI/BamHI sites of pHK412 to yield pALM11. The construction of pHK412, another pBR322 derivative, is described in European Patent Application 0,162,738 dated Nov. 27, 1985 (referred to therein as pHK412). DNA from both pALM3 and pALM11 were digested with PstI and XhoI. The resulting 1840 bp fragment of pALM11 and 3670 bp fragment of pALM3 were purified and ligated with T4 DNA ligase. The plasmid formed, pALM10, lacks all of the gIII gene (including 235 bp of upstream DNA) except for 186 bp encoding the carboxy-terminus portion. It also retains the tac promoter/operator and translation elements of the pALM3 expression vector. It produces no proteins upon induction (FIG. 4, lane 4).

CONSTRUCTION OF RECOMBINANT PSEUDORABIES WITH DELETIONS IN THE gIII GENE

1. PRV-2

Recombinant pseudorabies virus PRV-2 were produced as follows. The DNA of pALM2 was digested by incubating it with the restriction enzyme NcoI. One µg of the resulting NcoI digested DNA from pALM2 was cotransfected with 2 µg of DNA from parental (unaltered) PRV DNA into PK15 cells employing the procedure described by Graham et al., Virology, 52: 456–467 (1973). The transfected cells were incubated for 4 hours at 37°, washed with growth medium, and subjected to a (15% glycerol) shock for three minutes. The cells were again washed with medium, two times, and then placed into a fresh batch of growth medium. Twelve hours later, gIII monoclonal antibodies M1 and M16 (to a concentration of 0.6 µg/mL of each) and guinea pig complement (to a concentration of 5%) were added to enrich for gIII-defective recombinant virus. In the presence or absence of complement, these monoclonal antibodies neutralize the infectivity of parental PRV, but they do not neutralize PRV that no longer express gIII protein or that express truncated forms of the gIII glycoprotein. Neither M1 nor M16 monoclonal antibodies reacted with the gIII protein expressed by PRV-2. The total virus yield from each transfection was harvested when complete cytopathic effect was observed, which occurred after approximately 36 hours. Aliquots of the collected virus-containing fluid were diluted and plated out on PK15 cells to form plaques. The black plaque assay described by Smith et al., J. Immunol. Methods 40: 297–305 (1981) was applied to screen those plaques that did not react with the the M1 and M16 monoclonal antibodies. Plaques that failed to react with the antibodies (i.e. were white) were picked and twice purified by single plaque isolation prior to subsequent analysis. PRV-2 consists of the progeny of one such isolated plaque.

2. PRV-10

PRV-10 recombinant viruses, were produced and selected essentially as PRV-2 described above except that pALM10 was linearized with PstI and cotransfected with parental virus DNA.

3. Analysis of PRV-2 and PRV-10

Figure 5:
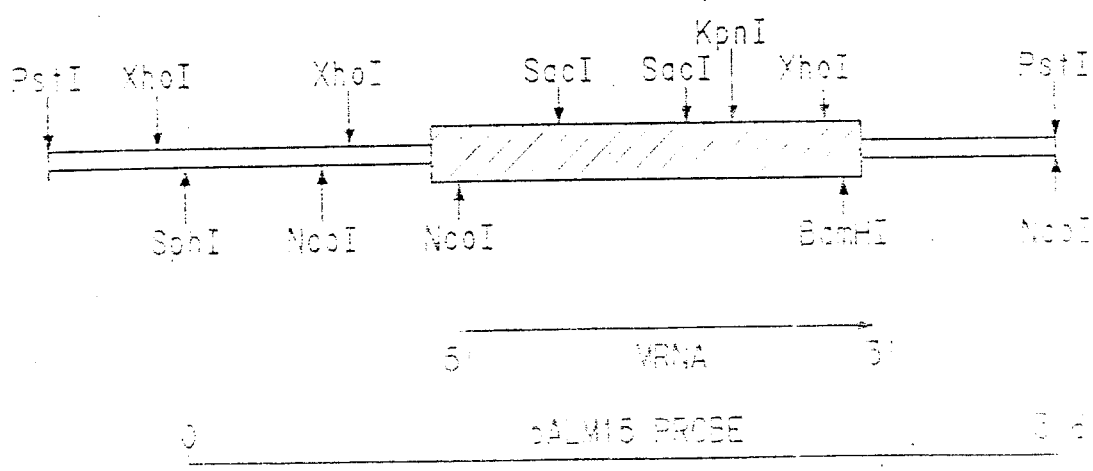

The DNA of PRV-2 and PRV-10 were analyzed to show that the deletions defined by pALM2 and pALM10 had been crossed into the selected viruses. Parental PRV was also analyzed for comparison. Viral DNA was isolated from nucleocapsids as described in the General Procedures. The DNA was digested with PstI and XhoI, fractionated on a 1% agarose gel, transferred to nitrocellulose and hybridized with a $^{32}$P-labelled probe from pALM15 (FIG. 5). As shown in the restriction enzyme map of the parental genome included in FIG. 5, the gIII gene is located approximately in the center of a 4.3 kb PstI fragment. There are three XhoI sites in this PstI fragment: two upstream of the gene and one within the gIII coding sequence near the carboxy terminus. The 1.48 kb XhoI fragment defined by the site 230 bp upstream of the gIII gene and the site within the gIII gene is the critical fragment for this analysis. Using $^{32}$P-labelled pALM15 as a probe, the patterns in the gel in FIG. 5 are observed. The parental pattern is shown in lane 1. Note the two fragments of 1.3 kb and 0.95 kb and the 1.48 kb internal XhoI fragment. DNA from PRV-2 (lane 2 in FIG. 5) which contains a 402 bp deletion within the gIII gene, the 1.3 kb and 0.95 kb fragments are unchanged, but the 1.48 kb internal XhoI fragment now migrates as a 1.1 kb fragment. Similarly, DNA from PRV-10 (lane 3 in FIG. 5) which contains a precise deletion of the 1.48 kb internal XhoI fragment shows only the 1.3 and 0.95 kb fragments.

Since the DNA of PRV-2 and PRV-10 are lacking 402 bp and 87% of gIII, respectively, yet PRV-2 and PRV-10 still infect and replicate normally, it is concluded that the gIII gene of PRV or the protein products thereof are not required for the infectivity and replication of the virus. In addition, the deletion of the region from the XhoI site immediately upstream from the gIII gene to the gIII does not result in curtailment of viral replication. Thus these portions of the PFV genome can be deleted and genes or fragments of genes placed properly in the place of gIII should be expressed and their products produced during viral replication in infected cells. Thus plasmids such as pALM2, pALM10 and pALM20 can be used as starting materials for making recombinant PRV viruses.

EXAMPLE 1

CONSTRUCTION OF A RECOMBINANT PRV CONTAINING AN HTLVIII ENVELOPE-CODING FRAGMENT OF DNA.

1. Preparation of a phosphorylated SacI/BglII linker.

The SacI/BglII linker is shown below.

5' GAGCTCAATGAGTCCGA 3'
3' CTCGAGTTACTCAGGCTCTAG 5'

The following were added to an appropriate reaction vessel:

4.0 µL annealed linker polynucleotides
5.5 µL of water
1.0 µL of 10x linker kinase buffer (700 mM tris-HCl, pH 7.6, 100 mM MgCl$_2$, 50 mM dithiothreitol)
1 µL 10 mM ATP, pH 7.0
2 uL T4 kinase (from Bethesda Research Laboratory (BRL)), Gaithersburg, Md., 20 units)

The mixture was incubated for 1 hour at 37°, and then heated at 65° for 5 minutes.

2. Preparation of a BglII 1.43 kb HTLVIII DNA fragment from bp 7198 to bp 8628 (a portion of the HTLVIII envelope polyprotein gene coding region)

The complete nucleotide sequence of the HTLVIII DNA is given in Ratner et al., Nature 313: 277–284 (1985). The plasmid pLORO provided the source of the HTLVIII nucleotides, although any source would be suitable. pLORO contains the fragment of the HTLVIII envelope polyprotein gene coding region from bp7196–bp8621. Included within this fragment are 135 bp of glycoprotein 120 (gp120) and all of glycoprotein 41 (gp41), the latter consisting of 1425 bp.

An HTLVIII fragment obtained from λBH10 by BglII digestion and cloned into the unique BglII site of plasmid pEXC, forming pLORO-1. pEXC was constructed by combining a PstI-BglII fragment from pΔROP and a PstI fragment from pKGP36.trp. pΔROP is a derivative of pBR322 in which a BglII linker has been inserted into the PvuII site. To create pKGP36.trp, the tryptophan (trp) promotor-operator and Shine-Delgarno sequences derived from pLD102, as described in Christie et al. J. Mol. Biol., 143: 335–341 (1980), were inserted into the ClaI site of plasmid pBR322.

Three aliquots (400 μl in each) of pLORC-1 DNA (1.2 μg were then digested with 100 units of BglII for 3 hours at 37° C. The DNA was precipitated by adding ethanol and resuspended in 20 μl of TE buffer (10 mm tris-HCl, pH 7.8, 1 mm disodium EDTA) and electrophoresed on an 0.8% agarose/TBE buffer gel for about 16 hours at 30 volts. TBE buffer consists of 50 mM tris-HCl, pH 8.2, 50 mM borate and 2.5 mM disodium EDTA. The gel was stained by immersion in a solution of ethidium bromide (1 μg/mL). Bands of DNA were visualized using U.V. light. A 1.43 kb band was excised from the gel and the fragment of DNA associated with the gel recovered by electroelution into 7.5 M ammonium acetate for 20 minutes at 100 volts. The BglII 1.43 kb HTLVIII DNA fragment was precipitated with the addition of 2.5 volumes of ethanol and resuspended in 15 μL of TE buffer.

3. Ligation of BglII 1.43 kb HTLVIII DNA fragment with kinased SacI/BglII linker.

The kinased SacI/BglII linker was ligated onto the HTLVIII fragment as follows. Added to an appropriate reaction vessel were:
  15 μL of DNA fragment in TE buffer (from part 2, above)
  11.5 μL 5x ligase buffer (500 mM tris-HCl, pH 7.8, 10 mM MgCl₂, 100 μg/mL bovine serum albumin)
  6 μL 10 mM ATP, pH 7.0
  22.5 μL 40% polyethylene glycol, molecular weight size 8000
  5 μL kinased linker
  5 μL water
  1 μL T4 DNA ligase (BRL, 1 unit)

Figure 6:
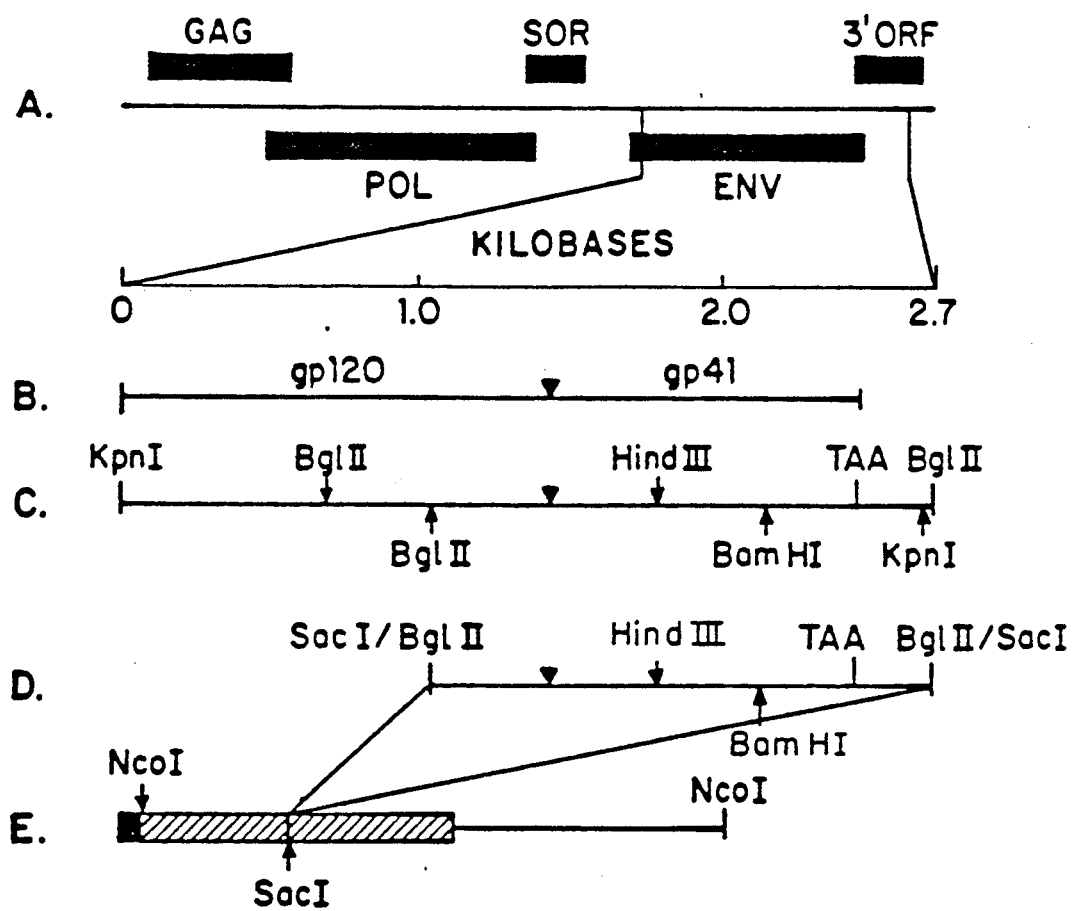

The mixture was incubated about 16 hours and the resulting DNA ethanol precipitated and resuspended in 10 μL of TE buffer. The DNA was then digested with 100 units of SacI for 3 hours at 37° in a total volume of 100 μL. The resulting HTLVIII-linker DNA fragment was ethanol precipitated and resuspended in 10 μL of TE buffer. This fragment is illustrated in FIG. 6(D).

4. Ligation of HTLVIII-linker DNA fragment with pALM2 to produce pALM 24

To an appropriate reaction vessel was added:
  0.2 μL of SacI digested pALM2 (0.07 ug)
  5 μL of the BglII 1.43 kb HTLVIII fragment with kinased SacI/BglII linker attached (prepared in part 3, above)
  2.3 μL water
  1 μL of 10x ligase buffer
  1 μL 10 mM ATP, pH 7.0
  0.5 μL ligase (New England Biolabs, Beverly, Mass., 1 unit)

This mixture was incubated at 12° for 2 days. The point of insertion of the HTLVIII-linker fragment into the gIII portion of pALM2 is illustrated in FIG. 6(E).

5. Selection of expression plasmid pALM24

A 200 μL aliquot of competent *E. coli* strain NF 1829 was mixed under transformation procedures described in Maniatis et al., Molecular Cloning, A Laboratory Manual, Cold Spring Harbor Laboratory, Cold Spring Harbor, N.Y. (1982), with 5 μL of the pALM24 mixture described in part 4 above. Aliquots of the transformed bacteria were plated on L-agar plates containing ampicillin (25 μg/mL). The inoculated plates were incubated about 16 hours at 37°. A resulting transformant was replated on an agaL-containing petri dish containing LB-ampicillin (10μg/mL). Plasmid DNA was prepared from cultures of the isolated cloned transformed bacteria. The plasmid is designated pALM24 (FIG. 6E).

6. Analysis of the pALM24 construct

DNA (20 μL) from pALM24 was digested with 30 units of SstI in a total of 100 μL for 2 hours at 37°. The resulting DNA was precipitated with ethanol resuspended in 10 μL of TE buffer and electrophoresed through an 0.8% agarose/TBE gel for about 16 hours at 30 volts. The gel was stained with ethidium bromide as previously described and the presence of the 1.43 kb band of DNA (HTLVIII DNA-linker fragment) verified. The orientation of the cloned fragment was checked by digesting 20 μL of the plasmid DNA with 40 units of HindIII in a total volume 100 μL for 2 hours at 37°. The DNA was precipitated with ethanol, resuspended in 20 μL of TE buffer and electrophoresed as described. The presence of a band of DNA with 1000 bp shows that the cloned fragment was in the correct orientation and that the construction was complete.

7. Production of recombinant PRV-24

Recombinant PRV-24 was produced essentially as described above for the production of PRV-2 and PRV-10 except that the source of DNA used to transfect PK15 cells were obtained from pALM24 cut with NcoI and parental PRV. Recombinant viruses were enriched by incubating the infected cultures in the presence of guinea pig complement and M1 and M16 monoclonal antibodies as previously described. Recombinant viruses were selected by means of the black plaque selection technique previously described. About 4 white plaques were selected from the approximately 18,000 total plaques (white and black) which appeared. One of the resulting white plaques was then purified by two successive single plaque isolations and grown into a stock of virus, PRV-24.

8. The production of a PRV-24 gIII/HTLVIII fusion protein with antigenic sites reactive against antibodies to HTLVIII To prove that PRV-24 contained and expressed HTLVIII glycosylated antigen PRV-24 as well as PRV-2 and PRV were separately grown in PK15 cells in the presence of 0.5 mCi of $^3$H-glucosamine. At 16 hours post-infection, the cells were scraped into phosphate buffered saline and collected by centrifugation. The infected cells were lysed by suspending them in RIPA buffer (150 mM NaCl, 10 mM tris, pH 7.9, 1% Triton X100, 1% deoxycholate, 0.1% sodium dodecyl sulfate) containing phenylmethylsulfonyl fluoride at a concentration of 100 μg/mL. Triton X100 is obtained from Sigma Chemical Company, St. Louis, Mo. The lysed cells and suspending fluid were then centrifuged at 100,000 x g for 30 minutes. To 400 μL of supernatant fluid from each of the samples were added in separate tubes, 20 μL of 490 serum (a polyclonal antiserum to the gIII protein of PRV, raised in rabbits against the Cro-PRV gIII fusion protein expressed by pALM3), 10 μL of antisera raised against the protein produced by a BglII to BamHI fragment of the HTLVIII gene from bp 7198 to 8052, as described in Ratner et al., Nature 313:277–284 (1985) containing a portion of the gp120 and the gp41 gene (anti-HTLVIII serum), and 20 μL of M2 antibody (against the gII family of PRV glycoproteins). The mixtures were incubated for 90 minutes on ice. Staph A (at 5X the volume of each antibody) was added to each, followed by a 15 minute incubation on ice. The mixtures were then washed with buffer B (120mM NaCl, 50mM Tris, pH 8.0, and 0.5% Nonidet P40 from Sigma Chemical Co.), then buffer B containing 1 M LiCl and finally, buffer B again. Pelleted Staph A's, resulting from centrifugation, were collected at each step. The recovered pelleted Staph A's were resuspended in 25 μL of SB (3% sodium dodecyl sulfate, 700 mM 2-mercaptoethanol, 10 mM tris buffer pH 6.8, 1% glycerol plus bromophenol blue) and boiled 2 minutes. The Staph A's were pelleted by centrifugation and the supernatant then electrophoresed on a 10% polyacrylamide/SDS gel. The gels were then fixed in methanol/acetic acid, washed twice in H₂O and then treated for 30 minutes in 1M sodium salicylate. The gels were dried and exposed on Kodak XAR5 film for one week using an intensifying screen.

Figure 7:
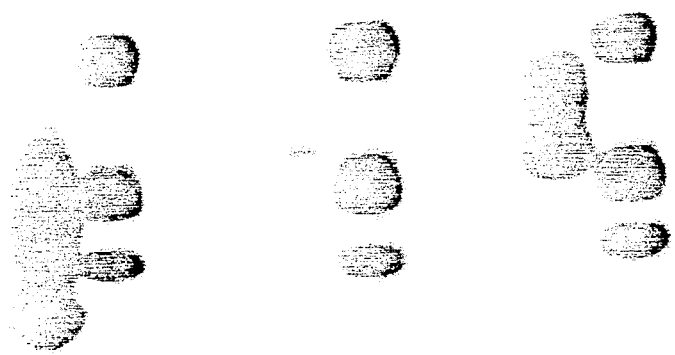

As shown in FIG. 7, specific glycoproteins of approximately 105,000 and 80,000 kilodaltons were precipitated from the lysates of PRV-24 by both the Serum 490 and the anti-HTLVIII serum. These proteins were not precipitated from the lysates of the parental PRV virus by Serum 490, however this serum did immunoprecipitate gIII specific proteins of 92,000 and 74,000 apparent molecular weight. The anti-HTLVIII serum failed to precipitate any proteins from the parental PRV lysates. This shows that PRV-24 produces a PRV gIII/HTLVIII fusion protein with antigenic sites reactive against both antibodies to gIII and HTLVIII.

9. Analysis of the PRV-24 genome

Figure 8:
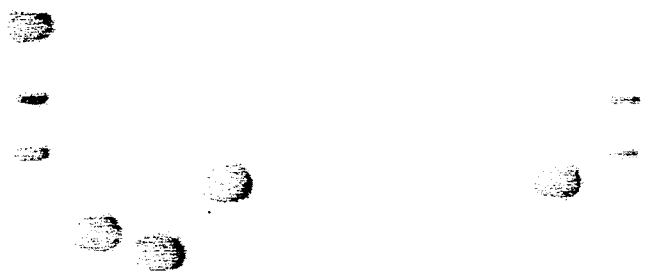
Figure 10:
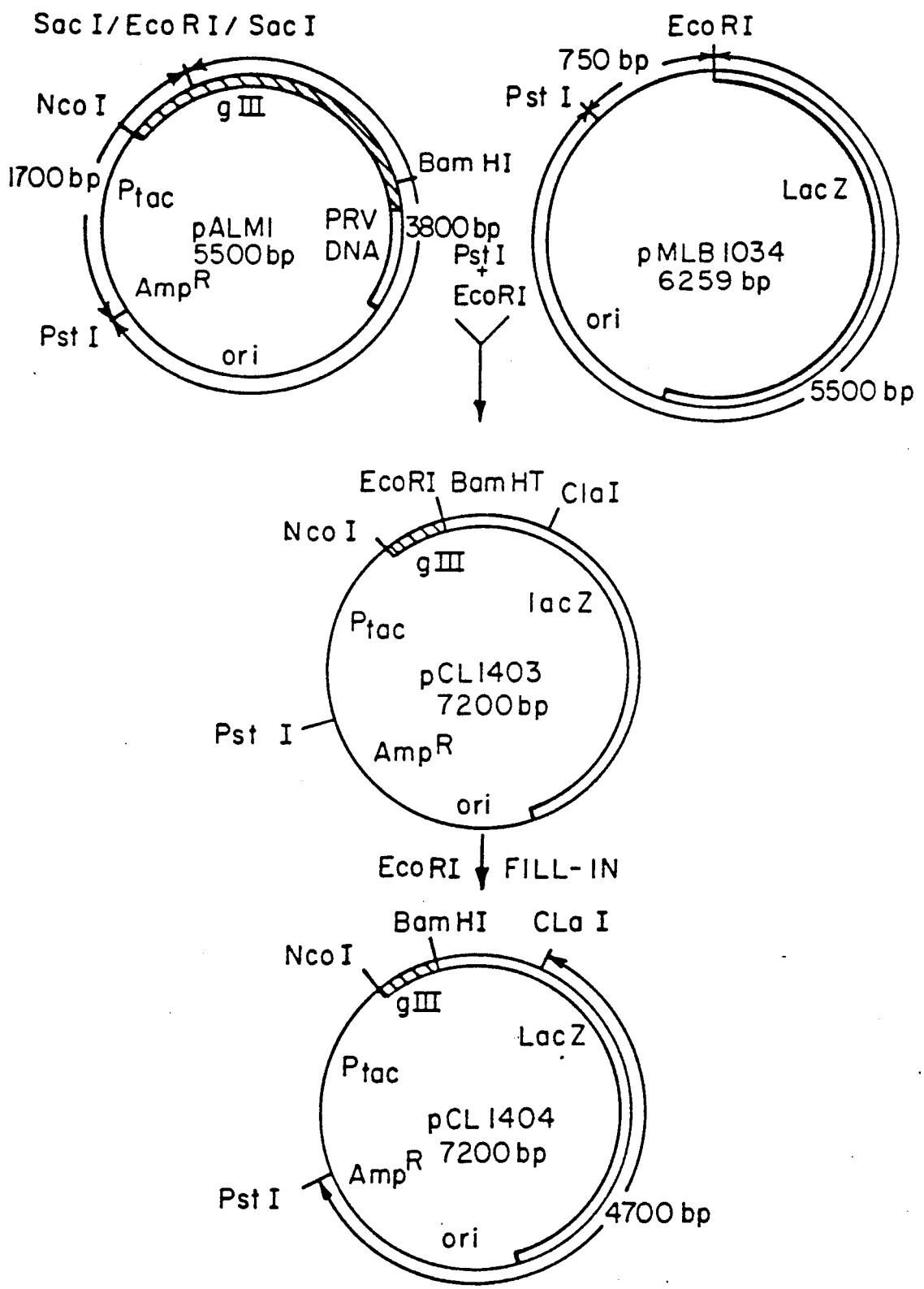
FIG. 10 shows plasmids pALM1, pMLB1034, pCL1403 and pCL1404. The figure depicts the route of construction of pCL1404.

Additionally, it was shown that PRV-24 contains the DNA sequence encoding a portion of the HTLVIII env gene. DNA was isolated from virions of parental PRV, PRV-2 and PRV-24 as described above. Each DNA (6 μg) was digested with PstI. The digested DNA was electrophoresed in two sets of three on a 1% agarose TEA (tris, EDTA, sodium acetate) gel in TEA. Southern Blot analysis was carried out as described earlier. After the DNA was transferred to nitrocellulose, the nitrocellulose was cut in half yielding two identical blots. One blot was hybridized with a gIII specific probe, pALM15. The other blot was hybridized with an HTLVIII specific probe, a KpnI fragment from bp 5928 to 8596 of the HTLVIII genome, as described in Ratner et al., Nature, 313: 277-284 (1985). The blot was exposed to Kodak XAR film, using an intensifying screen, at −70° C. for 2 days. The results are shown in FIG. 8. The autoradiogram of the blot using gIII as a probe showed hybridization to a PRV-24 DNA species of 5.3 kb. This DNA species is 1 kb larger than parental PRV DNA and 1.4 kb larger than PRV-2 DNA. This corresponds to the anticipated fragment size for the inserted HTLVIII DNA sequence. More importantly, the second blot using the HTLVIII probe only showed specific hybridization to a 5.3 kb species in the PRV-24 lane. No specific hybridization was seen to either parental PRV or PRV-2. This indicates that PRV-24 contains HTLVIII envelope sequences inserted with the gIII coding sequence.

EXAMPLE 2

CONSTRUCTION OF A RECOMBINANT PRV CONTAINING AN EcoRI SITE

1. Production of pALM1

5 This example describes the insertion of a novel EcoRI restriction enzyme site into the SacI restriction enzyme site of pALM2 generating plasmid pALM1. These experiments show that although PRV contains no EcoRI sites in its DNA genome, the presence of an EcoRI site is not detrimental to virus growth in tissue culture. This example further illustrates the making and using of plasmid pALM1 as a convenient EcoRI vector in which to place foreign genes for their subsequent transfer to PRV.

To produce a vector with a unique EcoRI site in the SacI site of the gIII gene, it was necessary to first rid pALM2 of its EcoRI site (see FIG. 9). Consequently, pALM2 was digested with EcoRI at 37° for 60 minutes. The reaction mixture was then incubated with the Klenow fragment of DNA polymerase I in the presence of all four deoxyribonucleotides to fill in the ends of the DNA. The blunt ends of the resulting DNA were then rejoined. This derivative of pALM2, free of any EcoRI sites is named pALM7. pALM7 DNA was digested with SacI at 37° for 60 minutes. The polynucleotide linker fragment consisting of 5′ CGAATTCGAGCT 3′ was synthesized on an Applied Biosystem DNA synthesizer using standard phosphoramidite chemistry and purified by reverse-phase high performance liquid chromatography. The linker DNA was melted at 68°, reannealed slowly and then phosphorylated using T4 polynucleotide kinase. The phosphorylated linker was then ligated to the SacI digested pALM7 DNA with T4 DNA ligase to create pALM1, shown in FIG. 10. The structure of pALM1 was verified by restriction enzyme and DNA sequence analysis. This linker maintains the reading frame of the truncated gIII protein as indicated by the spacing (see FIG. 10) and also introduces an EcoRI site bracketed by SacI sites. The linker adds 4 extra amino acids to the truncated gIII protein. It produced the expected fusion protein upon induction of *E. coli* bearing the pALM1 plasmid.

2. Production of Recombinant PRV-1 To prove that PRV can to tolerate an EcoRI site, PRV with the EcoRI site was produced by cotransfecting PK15 cells with parental PRV DNA and pALM1 DNA as described above for PRV-2. Virus defective for the gIII gene product was selected, isolated and characterized again in the same manner. One such isolate was designated PRV-1. PRV-1 was then grown in tissue culture. No deleterious effects of the EcoRI site on virus reproduction were observed.

EXAMPLE 3

CONSTRUCTION OF A RECOMBINANT PRV CONTAINING THE E. COLI GENE ENCODING BETA-GALACTOSIDASE

This example demonstrates the construction of a hybrid gIII gene and the *E. coli* gene encoding beta-galactosidase (the lacz gene) and the expression and glycosylation of a fusion protein containing a gene product not normally glycosylated. Further, the example shows the use of EcoRI sites engineered into the gIII gene.

1. Production of pCL1407 pALM1 DNA contains a truncated gIII gene with a synthetic EcoRI site as described in Example 2. The source of the lacz DNA sequence is the *E. coli* derived plasmid pMLB1034, a plasmid that contains a unique EcoRI site at the beginning of the lacz coding sequence. pMLB1034 is described in T.J. Silhavy, M.L. Berman, and L.W. Enquist, Experiments With Gene Fusions, pp. 250–251 (Cold Spring Harbor Laboratory 1984). pALM1 DNA is digested with the enzymes EcoRI and PstI and ligated to pMLB1034 plasmid DNA which has also been digested with PstI and EcoRI (FIG. 9). The ligation of a 5.5 kb PstI-EcoRI fragment from pMLB1034 to a 1.7 kb PstI-EcoRI fragment from pALM1 gave rise to a 7.2 kb plasmid pCL1403. While the lacZ gene is fused to the gIII gene at the EcoRI site in pCL1403, the two genes are not in the same reading frame. A protein coded from such a construction would thus result in a nonsense fusion protein. Four nucleotide pairs (NTP's: T-T-A-A) were therefore added to place the two genes in the same frame. This was accomplished by digesting pCL1403 DNA with EcoRI and filling in the resulting single stranded ends left by the EcoRI cleavage by incubating the digested DNA with the Klenow fragment of DNA polymerase I and the four deoxynucleotides. The blunt ends were ligated by means of T4 ligase creating pCL1404. This plasmid was selected by transforming *E. coli* strain NF1829 with the altered DNA containing pCL1404 and selecting ampicillin resistant colonies containing plasmid DNA resistant to digestion with EcoRI. One such single colony of bacteria was selected and served as the source of pCL1404. It was shown that bacteria containing pCL1404 produced a gIII-lacz fusion protein by growing colonies of the transformed bacteria on agar medium in the presence of 5-bromo-4-chloro-3-indoyl-beta-D-galactoside (x-Gal) and noting that the colonies were blue as a result of the beta- galactosidase activity. Also, bacteria containing PCL1404 grown in the presence of isopropyl-beta-D-thiogalactopyranoside (IPTG) produced a 130 kd protein when analyzed on a polyacrylamide/SDS gel.

Figure 11:
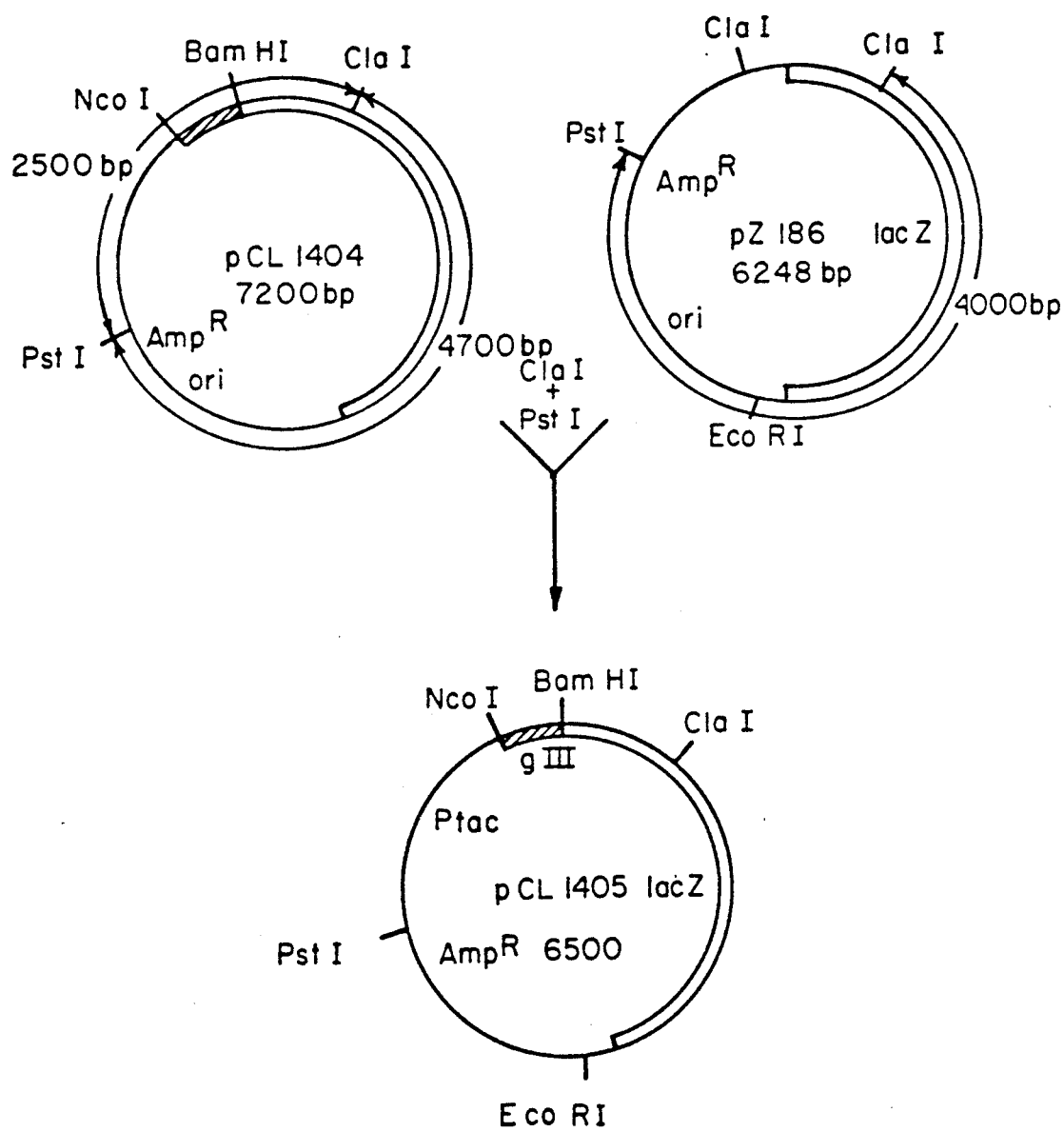
FIG. 11 shows plasmids pCL1404, pZ186 and pCL1405. The figure depicts the route of construction of pCL1405.
Figure 12:
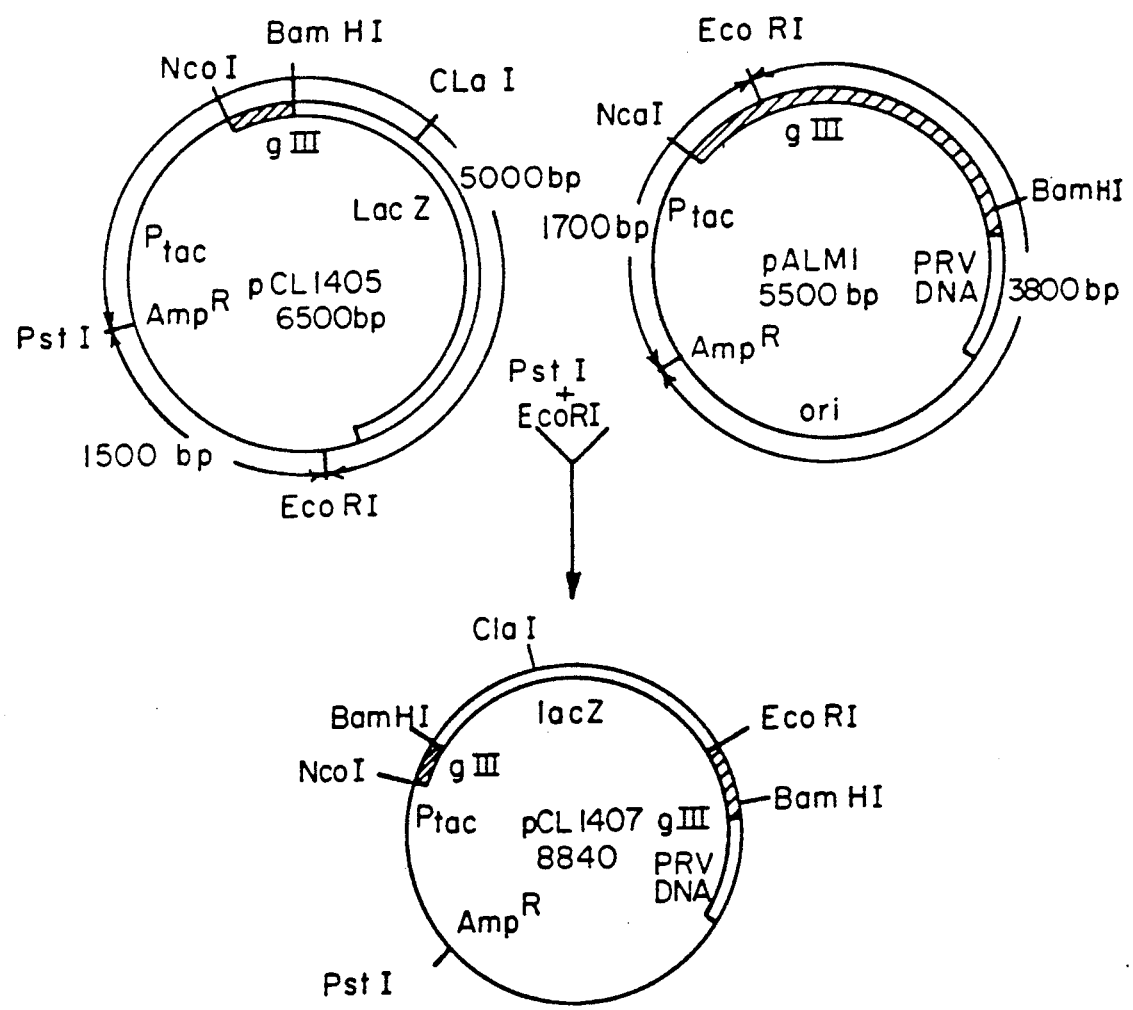
FIG. 12 shows plasmids pCL1405, pALM1 and pCL1407. The figure depicts the route of construction of pCL1407.

In order to replace the unaltered gIII gene with DNA containing the lacZ gene fused to gIII DNA, the DNA sequence containing the lacZ gene must be flanked by regions of DNA homologous to gIII sequences in the PRV genome. The NcoI-BamHI fragment of pCL1404 contains a gIII DNA sequence adjacent to and upstream of the lacZ gene. However there is no gIII DNA sequence adjacent to the downstream end of the lacZ gene. This was remedied as follows. First, pZ186, a pMLB524 derivative, was created. pMLB524, described in T.J. Silhavy, M.L. Berman, and L.W. Enquist, Experiments With Gene Fusions, pp. 28 (Cold Spring Harbor Laboratory 1984), was cleaved at its two PvuII sites and religated to form a single PvuII site. Into the PvuII site was then inserted a 4.3 kb lacz fragment obtained from a pMLB1010 AhaII digest. The plasmid pMLB1010 was obtained from Frederick Cancer Research Facility in Frederick, Md., however any source of lacz would suffice. Next, the 4.7 kb ClaI-PstI fragment of pCL1404, containing part of the lacZ gene and pBR322 sequences was replaced by a 4.0 kb ClaI-PstI fragment from the plasmid pZ186. This fragment from the plasmid pZ186 replaces the lacZ sequences and adds an EcoRI site after them. The resulting 6.5 kb plasmid was labelled pCL1405 (see FIG. 11). Then DNA from both pCL1405 and pALM1 plasmids were digested with EcoRI and PstI and the resulting DNA fragments ligated by means of T4 ligase. Resulting DNA plasmids were transformed into *E. coli* strain NF1829. Bacterial colonies resistant to ampicillin were recovered and analyzed for the presence of an 8.8 kb plasmid. This would represent the fusion of a 5.0 kb EcoRI-PstI fragment from pCL1405 with a 3.8 kb EcoRI-PstI fragment from pALM1. Bacteria containing such a plasmid were isolated and grown and the plasmid was termed pCL1407. (See FIG. 12) This plasmid now has gIII gene sequences adjacent to and flanking the lacZ gene. Using the techniques described in Example 1, DNA from pCL1407 was digested with NcoI and the resulting DNA along with the DNA from parental PRV were co-transfected into PK 15 cells. A recombinant virus containing an altered gIII gene was selected by previously described methods. Viruses from a representative viral plaque was isolated, purified and analyzed. The virus was designated PRV-Z1. By Southern analysis of the DNA of PRV-Z1, it was shown to contain a 3.0 kb insertion of lacZ specific DNA within the 4.3 kb PstI fragment containing the gIII gene. Immunoprecipitations of extracts of glucosamine labelled, PRV-Z1 infected cells with antisera against beta-galactosidase reveal the presence of a 130 kd gycosylated protein which is not present in cells infected with parental virus (See FIG. 13). Thus, cells infected with PRV-Z1 produce a glycosylated hybrid protein consisting of a small segment of gIII protein fused to beta-galactosidase.

EXAMPLE 4

CONSTRUCTION OF A RECOMBINANT PRV CONTAINING AN EcoRI SITE

This example describes the insertion of a synthetic EcoRI site into the KpnI site of the unaltered gIII gene and the construction of a PRV recombinant (PRV-32) containing this novel gene. The gIII protein produced from this novel gIII gene still reacts with monoclonal antibodies M1 and M16 in the black plaque test.

1. The Production of pALM 32 pALM3 was constructed as described above. This plasmid contains an EcoRI site just upstream of the tac promoter which was removed by cutting pALM3 DNA with EcoRI, filling in the single-stranded ends left by EcoRI cleavage using DNA polymerase 1 (see Example 2) and religating the linear plasmid with T4 ligase. The re-ligated DNA was transformed into *E. coli* strain NF1829 and plasmids were isolated that were resistant to cleavage by EcoRI. One such plasmid was isolated, characterized and named pALM-28 (See FIG. 14). There is a single KpnI site at position 993 bp in the gIII gene that consequently is the only KpnI site in pALM28. A synthetic DNA linker containing an EcoRI site of the following sequence was prepared:

5'- CAGAATTCGTAC -3'
3'- CTAGGTCTTAAG -5'

This linker was inserted into the KpnI site of pALM28 as described in Example 2 for linker insertion into the SacI site. The plasmid pALM32 was isolated that contains a single, unique EcoRI site at the KpnI site of the gIII gene. A KpnI site in pALM32 is also regenerated. The resulting gIII coding sequence now contains four additional codons as a result of the linker insertion.

2. Production of Recombinant PRV-32

The novel gIII gene in pALM32 was inserted by recombination into the DNA of PRV-2 using standard co-transfection as above. PRV-2 is described in Example 2. PRV-2 expresses a truncated gIII protein that does not react with M1 or M16 monoclonal antibodies. Therefore, PRV-2 makes white plaques in the "Black Plaque Test". After cotransfection of PRV-2 DNA and pALM32 DNA, black plaques were recovered at frequencies of about 0.5% of total plaques. Five black plaques were picked, purified and analyzed. Of the 5 virus isolates, two were analyzed and found to contain a novel EcoRI site at the KpnI site of gIII. One stock was chosen and called PRV-32. This example shows the construction of a PRV vector containing a synthetic EcoRI site in a full length gIII gene. The new gene expresses a gIII protein that reacts with M1 and M16 monoclonal antibodies in the "Black Plaque Test". Furthermore, this example teaches the utility of PRV vectors with gIII deletions (e.g. PRV-2 or PRV-10) as vehicles for insertion of gIII genes using the "Black Plaque Test" as a screen.

DEPOSIT OF MICROORGANISMS

The following viruses and plasmid have been deposited under the listed accession numbers with the American Tissue Culture Collection in Rockville, Md.:

|  | Accession No. |
| --- | --- |
| Virus |  |
| PRV-1 | VR 2142 |
| PRV-2 | VR 2143 |
| PRV-10 | VR 2144 |
| PRV-24 | VR 2145 |
| PRV-32 | VR 2146 |
| Plasmid |  |
| pALM20 (carried in E. coli NF1829) | 67151 |

The present invention is not to be limited in scope by the viruses deposited.

What is claimed is:

1. A recombinant pseudorabies virus comprising a foreign DNA fragment substituted for part of or the whole of a XhoI/gIII region of the viral genome wherein the foreign DNA fragment is capable of expression and codes for a desired protein.

2. A recombinant pseudorabies virus according to claim 1 wherein the foreign DNA fragment is a BglII 1.43 kb HTLVIII fragment.

3. A recombinant pseudorabies virus according to claim 2 wherein the virus is PRV-24 having a biological deposit accession number ATCC VR 2145.

4. A recombinant pseudorabies virus comprising deleting in whole or in part the XhoI/gIII region of the viral genome.

5. A recombinant pseudorabies virus according to claim 4 wherein the deletion in part begins at a first SacI restriction enzyme cleavage site within the gIII coding sequence of the viral genome and ends at a second SacI restriction enzyme cleavage site within the gIII coding sequence of the viral genome.

6. A recombinant pseudorabies virus according to claim 5 wherein the virus is PRV-2 having a biological deposit accession number ATCC VR 2143.

7. A recombinant pseudorabies virus according to claim 5 wherein an EcoRI restriction enzyme cleavage site is located at the regenerated SacI restriction enzyme cleavage site within the gIII coding sequence of the viral genome.

8. A recombinant pseudorabies virus according to claim 7 wherein the virus is PRV-1 having a biological deposit accession number ATCC VR 2142.

9. A recombinant pseudorabies virus according to claim 4 wherein the deletion in whole begins at a first XhoI restriction enzyme cleavage site and ends at a second XhoI restriction enzyme cleavage site within the gIII coding sequence of the viral genome.

10. A recombinant pseudorabies virus according to claim 9 wherein the virus is PRV-10 having a biological deposit accession number ATCC VR 2144.

11. A process for producing a desired protein comprising:
   (1) infecting a cell with a recombinant pseudorabies virus of claim 1;
   (2) culturing the infected cell until a desired protein is produced; and
   (3) recovering the protein.

12. A process according to claim 11 wherein the recombinant pseudorabies virus comprises a BglII 1.43 Kb HTLVIII fragment.

13. A process according to claim 11 wherein the recombinant pseudorabies virus is PRV-24 having a biological accession number ATCC VR 2145.

* * * * *